US009062205B2

(12) United States Patent
Reed et al.

(10) Patent No.: US 9,062,205 B2
(45) Date of Patent: Jun. 23, 2015

(54) ALKYL AMINE COMPOUNDS FOR FLUORESCENT LABELING

(75) Inventors: Michael W. Reed, Lake Forest Park, WA (US); Robert O. Dempcy, Kirkland, WA (US)

(73) Assignee: Blood Cell Storage, Inc., Seattle, WA (US)

( * ) Notice: Subject to any disclaimer, the term of this patent is extended or adjusted under 35 U.S.C. 154(b) by 0 days.

(21) Appl. No.: 13/482,528

(22) Filed: May 29, 2012

(65) Prior Publication Data

US 2012/0301880 A1 Nov. 29, 2012

Related U.S. Application Data

(60) Provisional application No. 61/491,107, filed on May 27, 2011, provisional application No. 61/650,304, filed on May 22, 2012.

(51) Int. Cl.

| | | |
|---|---|---|
| *C07D 311/82* | (2006.01) | |
| *C07D 321/00* | (2006.01) | |
| *C09B 11/24* | (2006.01) | |
| *C09B 62/44* | (2006.01) | |
| *C07F 9/6561* | (2006.01) | |
| *C07C 233/05* | (2006.01) | |
| *C07D 493/10* | (2006.01) | |
| *C12Q 1/68* | (2006.01) | |
| *C07H 21/00* | (2006.01) | |
| *B01L 3/00* | (2006.01) | |

(52) U.S. Cl.
CPC ............... *C09B 11/24* (2013.01); *C09B 11/245* (2013.01); *C09B 62/4401* (2013.01); *C07F 9/6561* (2013.01); *C07H 21/00* (2013.01); *C07C 233/05* (2013.01); *C07D 493/10* (2013.01)

(58) Field of Classification Search
CPC ...... C09B 11/08; C09B 11/24; C09B 11/245; C09B 62/4401
USPC ................ 549/200, 223; 530/300; 536/25.33, 536/26.6; 422/430; 435/6.1; 534/648
See application file for complete search history.

(56) References Cited

U.S. PATENT DOCUMENTS

| | | | |
|---|---|---|---|
| 7,608,460 | B2 | 10/2009 | Reed |
| 7,968,346 | B2 | 6/2011 | Reed |
| 8,148,167 | B2 | 4/2012 | Reed |
| 8,183,052 | B2 | 5/2012 | Reed |
| 8,497,134 | B2 | 7/2013 | Reed |
| 2012/0322161 | A1 | 12/2012 | Reed |

*Primary Examiner* — Jezia Riley
(74) *Attorney, Agent, or Firm* — Christensen O'Connor Johnson Kindness PLLC

(57) ABSTRACT

Alkyl amine dyes, oligonucleotide probes prepared from the alkyl amine dyes, phosphoramidites and solid supports prepared from the alkyl amine dyes, and methods of labeling biological agents using the alkyl amine dyes.

7 Claims, 8 Drawing Sheets

ALKYL AMINE COMPOUNDS FOR FLUORESCENT LABELING

CROSS-REFERENCE TO RELATED APPLICATION

This application claims the benefit of U.S. Provisional Application No. 61/491,107, filed May 27, 2011, and U.S. Provisional Application No. 61/650,304, filed May 22, 2012, each application expressly incorporated herein by reference in its entirety.

BACKGROUND OF THE INVENTION

The utility of alkyl amine modified fluorescent dyes is described in the Molecular Probes Handbook (9$^{th}$ Edition, Section 3.3 Derivitization Reagents for Carboxylic Acids and Glutamine). They offer a limited number of dyes for sale and the invention described here has the same inherent advantages. The novel molecular linker structures described here simplify single isomer synthesis and provide dye analogs with increased fluorescent brightness. Certain analogs have improved dye properties due to lower pKa and large Stokes shift.

The carboxylic acids of water-soluble biopolymers such as proteins can be coupled to hydrazines, hydroxylamines and amines in aqueous solution using water-soluble carbodiimides such as 1-ethyl-3-(3-dimethylaminopropyl)carbodiimide (EDAC). Including N-hydroxysulfosuccinimide in the reaction mixture has been shown to improve the coupling efficiency of EDAC-mediated protein-carboxylic acid conjugations. To reduce intra- and inter-protein coupling to lysine residues which is a common side reaction, carbodiimide-mediated coupling should be performed in a concentrated protein solution at a low pH, using a large excess of the nucleophile.

Peptide synthesis research has led to the development of numerous methods for coupling carboxylic acids to amines in organic solution. One such method involves the conversion of carboxylic acids to succinimidyl esters or mixed anhydrides. Dicyclohexylcarbodiimide and diisopropylcarbodiimide are widely used to promote amide formation in organic solution. Another recommended derivatization method for coupling organic solvent-soluble carboxylic acids, including peptides, to aliphatic amines without racemization is the combination of 2,2'-dipyridyldisulfide and triphenylphosphine.

Molecular Probes (Invitrogen) provides a wide selection of carboxylic acid-reactive reagents including several different Dapoxyl, ALEXA FLUOR, BODIPY, fluorescein, OREGON GREEN, rhodamine, TEXAS RED and QSY Hydrazine Derivatives, Hydroxylamine Derivatives and Amine Derivatives, all of which are particularly useful for synthesizing drug analogs and as probes for fluorescence polarization immunoassays. These probes all require a coupling agent such as a carbodiimide to react with carboxylic acids; they do not spontaneously react with carboxylic acids in solution. They do, however, react spontaneously with the common amine-reactive functional groups including succinimidyl esters and isothiocyanates.

A transglutaminase-catalyzed transamidation reaction of glutamine residues in some proteins and peptides enables their selective modification by amine-containing probes. This unique method for selective protein modification requires formation of a complex consisting of the glutamine residue, the aliphatic amine probe and the enzyme. It has been found that a short aliphatic spacer in the amine probe enhances the reaction. Although dansyl cadaverine D113 has been probably the most widely used reagent, ALEXA FLUOR cadaverines, OREGON GREEN 488 cadaverine, fluorescein cadaverine, tetramethylrhodamine cadaverine, TEXAS RED cadaverine and BODIPY TR cadaverine are among the most fluorescent transglutaminase substrates available. The intrinsic transglutaminase activity in sea urchin eggs has been used to covalently incorporate dansyl cadaverine during embryonic development.

Transamidation of cell-surface glutamine residues by the combination of a transglutaminase enzyme and a fluorescent or biotinylated aliphatic amine can form stable amides. Impermeability of the enzyme restricts this reaction to a limited number of proteins on the cell surface. This technique was used to selectively label erythrocyte band 3 protein with dansyl cadaverine and proteins of the extracellular matrix with fluorescein cadaverine.

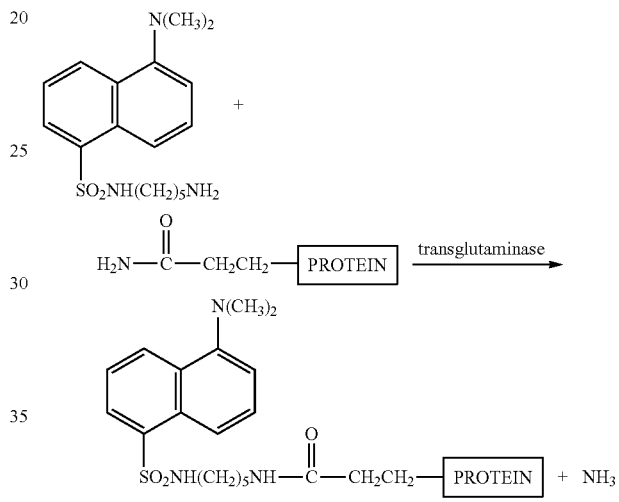

Transglutaminase-mediated labeling of a protein using dansyl cadaverine.

SUMMARY OF THE INVENTION

In one aspect, the invention provides alkyl amine compounds. In certain embodiments, the alkyl amine compounds have formula (I) or (II):

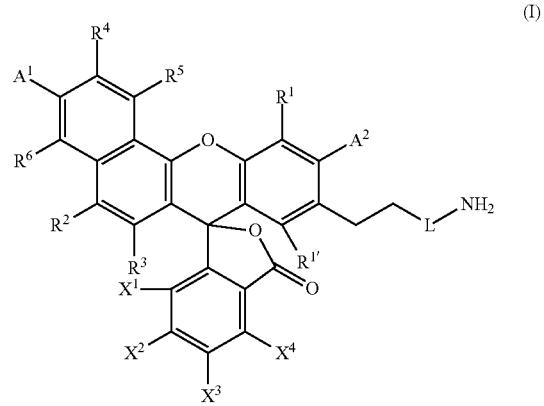

-continued

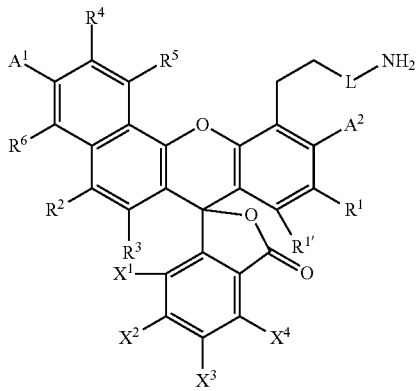
(II)

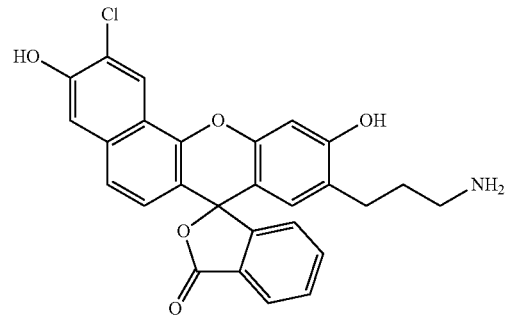 [SMILES: NCCCc1cc2c(cc1O)Oc1c(ccc3cc(O)c(Cl)cc13)C21OC(=O)c2ccccc21]

its salts, active esters, acid/base forms, and tautomers.

In another aspect, the invention provides alkyl amine compounds modified to include a functional group suitably reactive for covalently coupling the compounds of the invention to a variety of materials (e.g., surfaces and biomolecules such as proteins, peptide, oligonucleotides). In certain embodiments, the alkyl amine compounds have formula (III) or (IV):

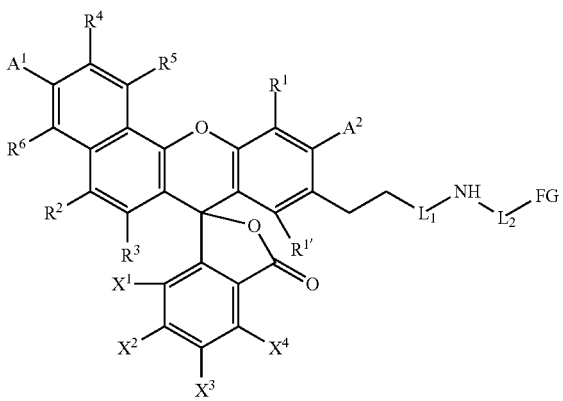
(III)

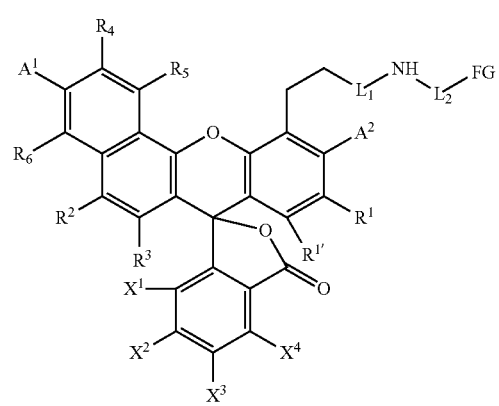
(IV)

their salts, active esters, acid/base forms, and tautomers, wherein $A^1$ and $A^2$ are independently selected from hydroxy, amino, mono- and dialkyl amino, protected hydroxy, protected amino, protected mono- and dialkyl amino, or when $A^1$ or $A^2$ is amino, mono- and dialkyl amino, $A^1$ and/or $A^2$ taken together with $R^2$ and/or $R^4$ (for $A^1$) or with $R^1$ (for $A^2$) and the atoms to which they are attached form a 5- or 6-membered nitrogen-containing ring;

their salts, active esters, acid/base forms, and tautomers, wherein $A^1$ and $A^2$ are independently selected from hydroxy, amino, mono- and dialkyl amino, protected hydroxy, protected amino, protected mono- and dialkyl amino, or when $A^1$ or $A^2$ is amino, mono- and dialkyl amino, $A^1$ and/or $A^2$ taken together with $R^2$ and/or $R^4$ (for $A^1$) or with $R^1$ (for $A^2$) and the atoms to which they are attached form a 5- or 6-membered nitrogen-containing ring;

$R^{1'}$, $R^1$, $R^2$, $R^3$, $R^4$, $R^5$, and $R^6$ are each independently selected from the group consisting of hydrogen, halogen, cyano, trifluoromethyl, $(C_1-C_8)$alkyl, $(C_1-C_8)$alkylthio and $(C_1-C_8)$alkoxy, aryl, and heteroaryl;

$X^1$, $X^2$, $X^3$, and $X^4$ are each independently selected from the group consisting of hydrogen, halogen, cyano, trifluoromethyl, $(C_1-C_8)$alkyl, $(C_1-C_8)$alkoxy, $(C_1-C_8)$alkylthio, $(C_2-C_8)$alkenyl, $(C_2-C_8)$alkynyl, aryl, aryl$(C_1-C_4)$alkyl, heteroaryl, $SO_3H$ and $CO_2H$, wherein the alkyl portions of any of $R^{1'}$ and $R^1$-$R^6$ and $X^1$-$X^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and wherein the aryl or heteroaryl portions of any of $R^{1'}$ and $R^1$-$R^6$ and $X^1$-$X^4$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy; and wherein L has a length not exceeding the length of a normal alkyl chain of 25 carbons and comprises from one to about 50 atoms.

In one embodiment, $R^4$ is a halogen. In another embodiment, $R^6$ is a halogen. In a further embodiment, $R^4$ and $R^6$ are halogens. For certain of these embodiments, $R^4$ and $R^6$ are chloro.

In one embodiment, the compound of formula (I) has the formula:

$R^{1'}$, $R^1$, $R^2$, $R^3$, $R^4$, $R^5$, and $R^6$ are each independently selected from the group consisting of hydrogen, halogen, cyano, trifluoromethyl, $(C_1-C_8)$alkyl, $(C_1-C_8)$alkylthio and $(C_1-C_8)$alkoxy, aryl, and heteroaryl;

$X^1$, $X^2$, $X^3$, and $X^4$ are each independently selected from the group consisting of hydrogen, halogen, cyano, trifluoromethyl, $(C_1-C_8)$alkyl, $(C_1-C_8)$alkoxy, $(C_1-C_8)$alkylthio, $(C_2-C_8)$alkenyl, $(C_2-C_8)$alkynyl, aryl, aryl$(C_1-C_4)$alkyl, heteroaryl, $SO_3H$ and $CO_2H$, wherein the alkyl portions of any of $R^{1'}$ and $R^1-R^6$ and $X^1-X^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and wherein the aryl or heteroaryl portions of any of $R^{1'}$ and $R^1-R^6$ and $X^1-X^4$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy;

wherein $L_1$ has a length not exceeding the length of a normal alkyl chain of 25 carbons and comprises from one to about 50 atoms, wherein $L_2$ has a length not exceeding the length of a normal alkyl chain of 25 carbons and comprises from one to about 50 atoms, and wherein FG is a functional group reactive toward and capable of covalently coupling the fluorescent dye compound to a suitably reactive material.

In one embodiment, the compound of formula (III) has the formula:

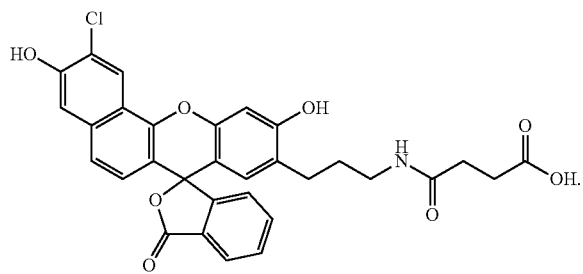 [SMILES: O=C(O)CCC(=O)NCCCc1cc2c(cc1O)Oc1c(ccc3cc(O)c(Cl)cc13)C21OC(=O)c2ccccc21]

its salts, active esters, acid/base forms, and tautomers.

In another aspect, the invention provides conjugates, comprising a biomolecule having one or more of a compound of formulae (I), (II), (III), or (IV) covalently coupled thereto.

In a further aspect, the invention provides a nucleic acid probe, comprising an oligonucleotide having one or more of a compound of a compound of formulae (I), (II), (III), or (IV) covalently coupled thereto. In one embodiment, the probe further includes a second fluorescent compound. In one embodiment, the second fluorescent compound has an emission spectrum that overlaps with the absorption spectrum of a compound of formulae (I), (II), (III), or (IV). In another aspect, the second fluorescent compound has an absorption spectrum that overlaps with the emission spectrum of the compound of formulae (I), (II), (III), or (IV). In one embodiment, the probe further includes a quencher moiety.

In another aspect, the invention provides a phosphoramidite prepared from a compound of formulae (I), (II), (III), or (IV).

In a further aspect of the invention, a method for determining the presence and/or amount of a nucleic acid in a sample is provided. In one embodiment, the method includes contacting a sample optionally containing a target nucleic acid with a probe of the invention capable of hybridizing to the target nucleic acid. In one embodiment, the probe is a hybridization probe or a hydrolysis probe.

In other aspects of the invention, kits are provided. In one embodiment, the kit includes one or more compounds of formulae (I), (II), (III), or (IV). In one embodiment, the kit includes one or more nucleic acid probes of the invention. In one embodiment, the probe is a hybridization probe or a hydrolysis probe.

In a further aspect, the invention provides an alkyne having the formula

wherein L is a linker moiety having a length not exceeding the length of a normal alkyl chain of 25 carbons and comprising from one to about 50 atoms, and wherein P is a nitrogen protecting group.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1:
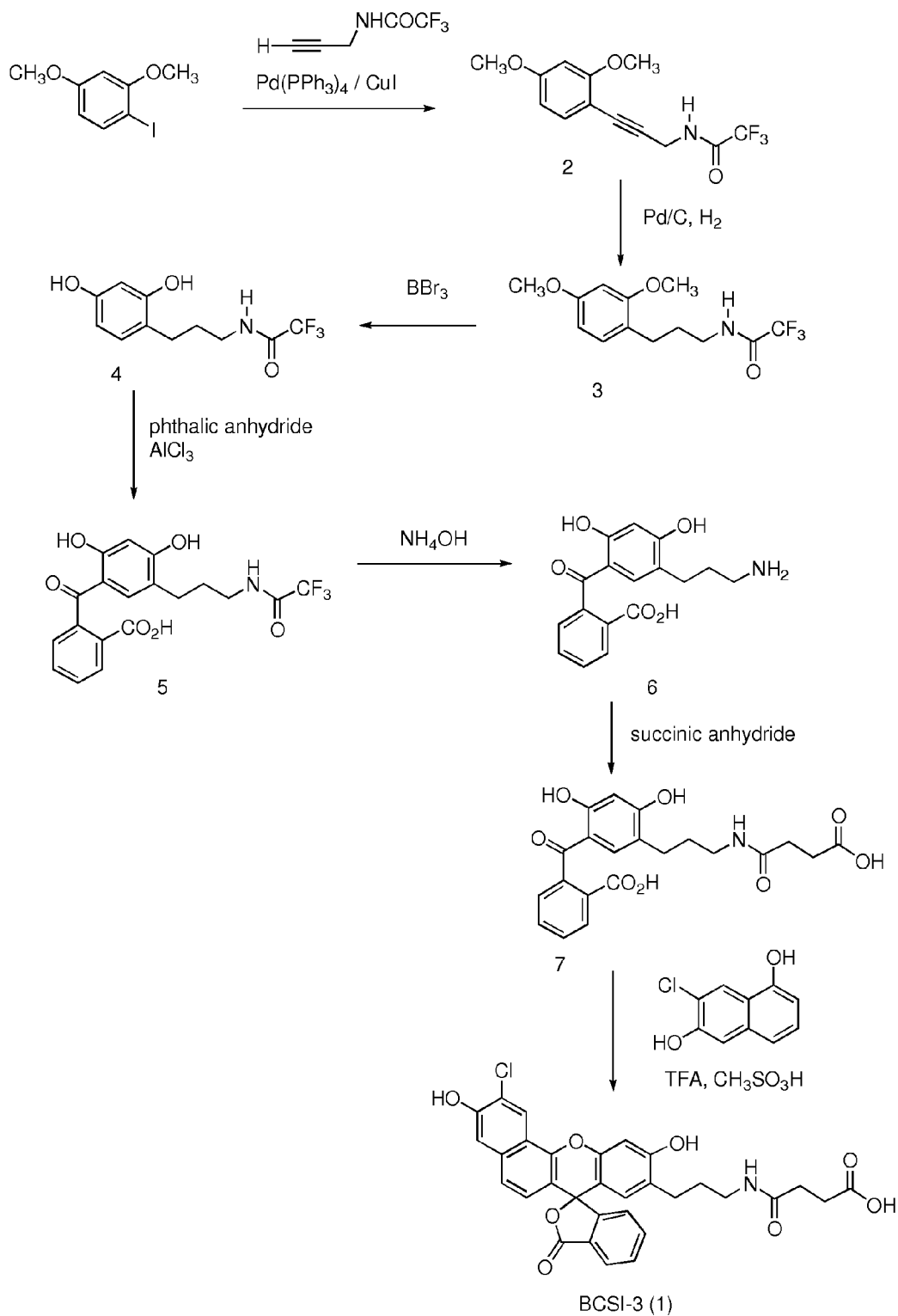
FIG. 1 illustrates the synthesis of a representative 2-halo seminaphthofluorescein compound (BCSI-3).

The present invention provides fluorescent dye compounds, methods for making the compounds, fluorescent dye-labeled compounds and biological agents, and methods for making fluorescent dye-labeled biological agents.

The compounds of the invention are described below. In one embodiment, the fluorescent dye compound of the invention is an alkyl amine compounds linker such as the 2-chloro seminaphthofluorescein shown below:

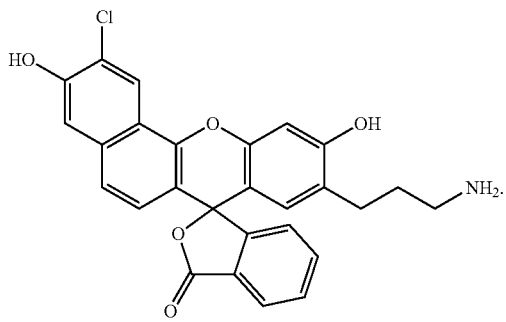 [SMILES: NCCCc1cc2c(cc1O)Oc1c(ccc3cc(O)c(Cl)cc13)C21OC(=O)c2ccccc21]

The alkyl amine compounds of the invention can be converted to carboxylic acid linker groups by reaction with succinic anhydride or similar bifunctional electrophiles to provide carboxylic acid compounds as shown below:

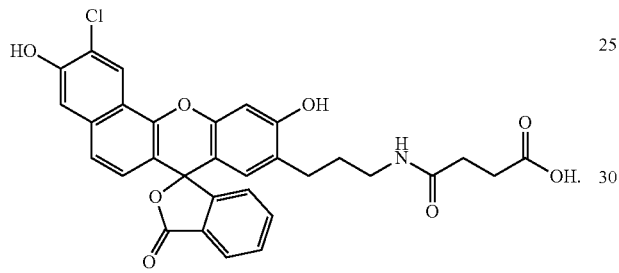

Carbodiimide activation of the carboxylic acid compounds allows for reaction with nucleophilic lysine residues in proteins to provide labeled proteins.

The alkyl amine compounds can also be used to prepare phosphoramidite or solid supports, as shown below, for the preparation of labeled DNA strands by automated synthesis:

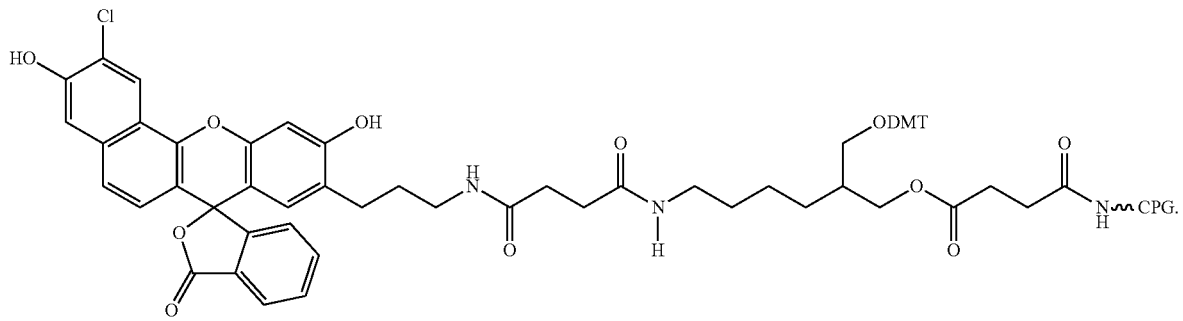

Another method for introducing the alkyl amine dyes is labeling of glutamine residues in proteins and peptides by transamidation as described above.

Preferred fluorescent alkyl amines derivatives are based on known dyes selected from the coumarins, benzocoumarins, xanthenes, benzo[a]xanthenes, benzo[b]xanthenes, benzo[c]xanthenes, phenoxazines, benzo[a]phenoxazines, benzo[b]phenoxazines and benzo[c]phenoxazines. Synthesis and properties of certain analogs are described in U.S. Pat. No. 6,972,339.

Xanthene, benzo[a]xanthene, and benzo[c]xanthene compounds of the invention are have applications in pH sensing devices and also have unique fluorescent spectral properties (large Stokes shift). The present invention provides three dye structures that can be excited with a single wavelength light source and multiplex detection accomplished by taking advantage of the variable Stokes shift described for the xanthene dyes (15-23 nm), benzo[a]xanthene dyes (27-40 nm) and benzo[c]xanthene dyes (77 nm). For example, the three dyes could be used to label three different fluorogenic DNA probe sequences and the single excitation wavelength simplifies instrumentation.

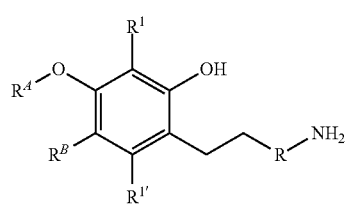

I

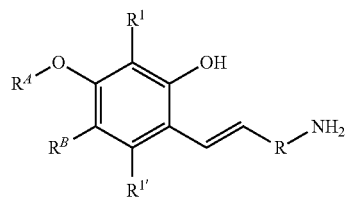

II

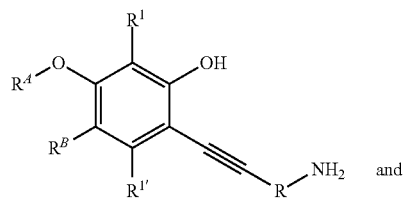

III and

-continued

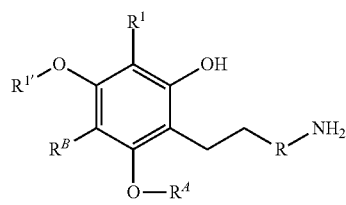

IV

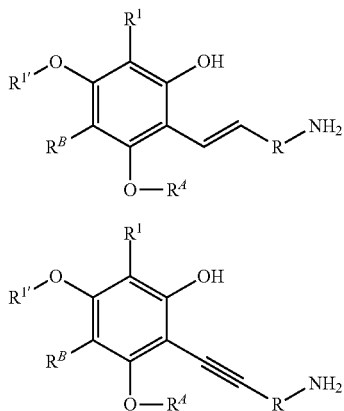

Functional groups and substituents for dye types I-VI above are defined in U.S. Pat. No. 7,601,851, expressly incorporated herein by reference in its entirety.

The xanthene, benzo[a]xanthene, and benzo[c]xanthene compounds of the invention are described below.

Unless otherwise stated, the following terms used in the specification and claims have the meanings given below:

The term "amine" refers to either a primary (—NH$_2$), secondary (—NHR) functional group where R is an alkyl group that does not hinder reaction with electrophilic acylating agents, biomolecules or enzyme catalysts (transglutaminase).

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, (C$_1$-C$_8$)alkyl is meant to include methyl, ethyl, n-propyl, 2-propyl, tert-butyl, pentyl, cyclopentyl, cyclopropylmethyl, and the like. For each of the definitions herein (e.g., alkyl, alkenyl, alkoxy, arylalkoxy), when a prefix is not included to indicate the number of main chain carbon atoms in an alkyl portion, the radical or portion thereof will have eight or fewer main chain carbon atoms.

The term "alkylene" means a linear saturated divalent hydrocarbon radical or a branched saturated divalent hydrocarbon radical having the number of carbon atoms indicated in the prefix. For example, (C$_1$-C$_6$)alkylene is meant to include methylene, ethylene, propylene, 2-methylpropylene, pentylene, and the like.

The term "alkenyl" refers to a linear monovalent hydrocarbon radical or a branched monovalent hydrocarbon radical having the number of carbon atoms indicated in the prefix and containing at least one double bond. For example, (C$_2$-C$_6$) alkenyl is meant to include, ethenyl, propenyl, and the like.

The term "alkynyl" refers to a linear monovalent hydrocarbon radical or a branched monovalent hydrocarbon radical containing at least one triple bond and having the number of carbon atoms indicated in the prefix. For example, (C$_2$-C$_6$) alkynyl is meant to include ethynyl, propynyl, and the like.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "aryl" means a monovalent monocyclic or bicyclic aromatic hydrocarbon radical of 6 to 10 ring atoms which is unsubstituted or substituted independently with one to four substituents, preferably one, two, or three substituents selected from alkyl, cycloalkyl, cycloalkyl alkyl, halo, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl alkyl, phenyl or phenylalkyl, aryl or arylalkyl), —(CR'R")$_n$—COOR (where n is an integer from 0 to 5, R' and R" are independently hydrogen or alkyl, and R is hydrogen, alkyl, cycloalkyl, cycloalkyl alkyl, phenyl or phenylalkyl aryl or arylalkyl) or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl, aryl or arylalkyl). More specifically the term aryl includes, but is not limited to, phenyl, biphenyl, 1-naphthyl, and 2-naphthyl, and the substituted forms thereof. Similarly, the term "heteroaryl" refers to those aryl groups wherein one or more heteroatoms or heteroatom functional groups have replaced a ring carbon, while retaining aromatic properties, for example, pyridyl, quinolinyl, quinazolinyl, thienyl, and the like. For brevity, the term aryl, when used in combination with other radicals (e.g., aryloxy, arylalkyl) is meant to include both aryl groups and heteroaryl groups as described above.

The term "arylalkyl" refers to a radical —R$^a$R$^b$ where R$^a$ is an alkylene group (having the indicated number of carbon atoms, or if unspecified having six or fewer main chain carbon atoms) and R$^b$ is an aryl group as defined herein. Examples of arylalkyl groups include benzyl, phenylethyl, 3-(3-chlorophenyl)-2-methylpentyl, and the like.

Similarly the term "arylalkenyl" means a radical —R$^a$R$^b$ where R$^a$ is an alkenylene group and R$^b$ is an aryl group as defined herein, e.g., 3-phenyl-2-propenyl, and the like.

"Arylheteroalkyl" means a radical —R$^a$R$^b$ where R$^a$ is an heteroalkylene group (having the indicated number of carbon atoms) and R$^b$ is an aryl group as defined herein, e.g., 2-hydroxy-2-phenyl-ethyl, 2-hydroxy-1-hydroxymethyl-2-phenyl-ethyl, and the like.

The term "aryloxy", refers to a radical —OR where R is an aryl group, e.g., phenoxy, naphthyloxy and the like.

The prefix "halo" and the term "halogen" when used to describe a substituent, refer to —F, —Cl, —Br and —I.

The term "heteroalkyl" refers to an alkyl radical as defined herein with one, two or three substituents independently selected from cyano, —OR$^a$, —NR$^b$R$^e$, and —S(O)$_n$R$^d$ (where n is an integer from 0 to 2), with the understanding that the point of attachment of the heteroalkyl radical is through a carbon atom of the heteroalkyl radical. R$^a$ is hydrogen, alkyl, aryl, arylalkyl, alkoxycarbonyl, aryloxycarbonyl, carboxamido, or mono- or di-alkylcarbamoyl. R$^b$ is hydrogen, alkyl, aryl or arylalkyl. R$^c$ is hydrogen, alkyl, aryl, arylalkyl, alkoxycarbonyl, aryloxycarbonyl, carboxamido, mono- or di-alkylcarbamoyl or alkylsulfonyl. R$^d$ is hydrogen (provided that n is 0), alkyl, aryl, arylalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, R$^a$, R$^b$, R$^c$, and R$^d$ can be further substituted by NH$_2$, fluorine, alkylamino, di-alkylamino, OH or alkoxy. Additionally, the prefix indicating the number of carbon atoms (e.g., C$_1$-C$_{10}$) refers to the total number of carbon atoms in the portion of the heteroalkyl group exclusive of the cyano, —OR$^a$, —NR$^b$R$^c$, or —S(O)$_n$R$^d$ portions.

The term "heterocyclic" refers to a saturated or unsaturated non-aromatic cyclic radical of 3 to 8 ring atoms in which one or two ring atoms are heteroatoms selected from O, NR (where R is independently hydrogen or alkyl) or $S(O)_n$ (where n is an integer from 0 to 2), the remaining ring atoms being C, where one or two C atoms may optionally be replaced by a carbonyl group. The heterocyclyl heterocyclic ring may be optionally substituted independently with one, two, or three substituents selected from alkyl, halo, cyano, hydroxy, alkoxy, amino, mono-alkylamino, di-alkylamino, haloalkyl, haloalkoxy, —COR (where R is hydrogen, alkyl, cycloalkyl, cycloalkyl-alkyl, phenyl or phenylalkyl aryl or arylalkyl), —(CR'R")$_n$—COOR (n is an integer from 0 to 5, R' and R" are independently hydrogen or alkyl, and R is hydrogen, alkyl, cycloalkyl, cycloalkyl-alkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, phenyl or phenylalkyl). More specifically the term heterocyclyl heterocyclic includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof. The prefix indicating the number of carbon atoms (e.g., $C_3$-$C_{10}$) refers to the total number of carbon atoms in the portion of the heterocyclyl heterocyclic group exclusive of the number of heteroatoms.

The terms "heteroalkylene" means a linear saturated divalent hydrocarbon radical of one to six carbons or a branched saturated hydrocarbon radical of three to six carbon atoms with one, two or three substituents independently selected from —OR$^a$, —NR$^b$R$^c$, and —S(O)$_n$R$^d$ (where n is an integer from 0 to 2) where, R$^a$, R$^b$, R$^c$, and R$^d$ are as defined herein for a heteroalkyl radical. Examples include, 2-hydroxyethan-1,2-diyl, 2-hydroxypropan-1,3-diyl, and the like.

Each of the above terms (e.g., "alkyl," "heteroalkyl," and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, heterocycloalkyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to four, preferably, zero, one, two or three substituents. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the alkyl groups will have from 0-3 substituents, more preferably 0, 1, or 2 substituents, unless otherwise specified.

Similarly, substituents for the aryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

Certain compounds or oligonucleotides of the present invention may exist in a salt form. Such salts include base addition salts such as sodium, potassium, calcium, ammonium, organic amino, or magnesium salt, or a similar salt. When the compounds or modified oligonucleotides of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts," Journal of Pharmaceutical Science, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention. The methods for the determination of stereochemistry and the separation of isomers are well-known in the art (see discussion in Chapter 4 of ADVANCED ORGANIC CHEMISTRY, 4th edition J. March, John Wiley and Sons, New York, 1992).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not (e.g., $^2$H), are intended to be encompassed within the scope of the present invention.

"Protecting group" or "protected form thereof" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 2nd ed. 1991), Beaucage and Iyer, Tetrahedron 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like (see also, Boyle, A. L. (Editor), CURRENT PROTOCOLS IN NUCLEIC ACID CHEMISTRY, John Wiley and Sons, New York, Volume 1, 2000). Representative hydroxy protecting groups include those where the hydroxy group is either acylated or alkylated such as benzyl and trityl ethers as well as alkyl ethers, tetrahydropyranyl ethers, trialkylsilyl ethers and allyl ethers. Additionally, hydroxy groups can be protected by photoremovable groups such as α-methyl-6-nitropiperonyloxycarbonyl (McGall, G. H. and Fidanza, J. A., Photolithographic synthesis of high-density olignucleotide arrays, in DNA ARRAYS METHODS AND PROTOCOLS, Edited by Rampal J. B., METHODS IN MOLECULAR BIOLOGY, 170:71-101 (2001), Humana Press, Inc., NY; Boyle, Ann L. (Editor), Current Protocols in Nucleic Acid Chemistry, John Wiley and Sons, New York, Volume 1, 2000).

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

The term "biological agent" refers to essentially any nucleoside, oligonucleotide, peptide, protein, aminocarbohydrate or ligand, as well as analogs thereof (e.g., oligonucleotides having modified or non-natural bases).

The term "conjugate" refers to a molecule formed by the covalent attachment of two or more components such as oligonucleotides, fluorophores, quenchers, minor groove binders, and the like.

"Oligonucleotide" and "polynucleotide" are used interchangeably and refers to a polymer of nucleotides, either natural or synthetic including, but not limited to those nucleotides having modified bases, sugar analogs, and the like. As noted above, an oligonucleotide conjugate will refer to an oligonucleotide as defined, having at least one covalently attached fluorophore, quencher, minor groove binder (MGB) or other useful fragments, as well as combinations of the recited components.

The term "solid support" refers to essentially any solid or semisolid matrix that is useful for, and compatible with, automated oligonucleotide techniques and includes, glass, polystyrene, nylon, plastic, combinations and the like. Examples of useful solid supports have been described in, for example, U.S. Pat. Nos. 5,262,530; 5,419,966; 5,512,667; and 5,589,586.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

The present invention provide a variety of fluorescent dyes (or fluorophores) can be prepared having a reactive linked alkyl amine functional group, providing reagents that are shelf-stable and that can be used to label essentially any biological agent (e.g., oligonucleotides, peptides, proteins, probes, and the like) due to their reactivity with suitable preferably nitrogen-containing electrophiles. Accordingly, the invention provides new "alkyl amine dyes" as well as methods of labeling biological agents using these "alkyl amine dyes". The invention further provides reagents such as phosphoramidite-derivatized dyes that can be prepared from the alkyl amine dyes described herein. Additionally, support-bound dyes, similarly prepared from the alkyl amine dyes are also provided.

The "alkyl amine dye" approach to labeling as well as reagent (e.g., support-bound dyes and phosphoramidites) has been found to be compatible with, for example, coumarin dyes, benzocoumarin dyes, fluorescein dyes, rhodamine and rhodol dyes, phenoxazine dyes, benzophenoxazine dyes, xanthene dyes, benzoxanthene dyes, and cyanine dyes.

Examples of these and other suitable dye classes can be found in Haugland, et al., HANDBOOK OF FLUORESCENT PROBES AND RESEARCH CHEMICALS, SIXTH ED., Molecular Probes, Eugene, Oreg. 1996; U.S. Pat. Nos. 5,187,288; 5,188,934; 5,227,487, 5,248,782; 5,304,645; 5,433,896; 5,442,045; 5,556,959; 5,583,236; 5,808,044;

5,986,086; 6,020,481; 6,162,931; and 6,221,604; Smith, et al., J. Chem. Soc. Perkin Trans. 2, 1993, 1195-1204; Whitaker, et al., Anal. Biochem. 207:267-279 (1992); Whitaker et al. Anal. Biochem. 194, 330-344 (1991) and Hirschberg, et al., Biochemistry 37:10381-10385 (1998).

Methods for Labeling Biological Agents

In one aspect, the present invention provides methods for preparing a fluorescent dye-labeled biological agent, the method comprising contacting an unlabeled biological agent with a fluorescent dye-linked alkyl amine derivative under conditions sufficient to covalently attach the fluorescent dye to said biological agent and form a fluorescent dye-labeled biological agent. The term "fluorescent dye-linked alkyl amine derivative" or more simply "alkyl amine dye" as used herein refers to essentially any fluorescent dye that has a reactive linked alkyl amine (e.g., nucleophilic or electrophilic forms of the dye). In most instances below, an alkyl amine linker arm is illustrated as an alkyl amine, although the invention is not so limited.

As noted above, the present invention finds broad application in labeling of nucleic acids (including nucleotides, nucleosides, DNA, RNA, PNA, locked nucleic acids, oligonucleotides and the like), peptides or proteins, oligosaccharides, glycosylated proteins, and other biological agents. Additionally, the nucleic acids can include modified bases (e.g., 5-substituted pyrimidines, 3-substituted purines, substituted deazapurines, substituted pyrazolo[3,4-d]pyrimidines, and the like). The invention also finds utility in labeling of oligonucleotides and modified oligonucleotides having attached groups such as minor groove binders, intercalators, crosslinking groups, and the like. DNA probes labeled with certain seminaphthofluorescein alkyl amine dyes can be used in medical diagnostic tests.

Reaction with Electrophiles.

As noted above, the invention is broadly applicable to the preparation and use of new alkyl amine derivatives of a variety of dyes. In many embodiments, reactive alkyl amine derivatives can be prepared by basic deprotection of trifluoroacetamide protected side chain linked alkyl amine) and reacted with electrophilic groups on macromolecular biological compounds ($R^M$) as illustrated below:

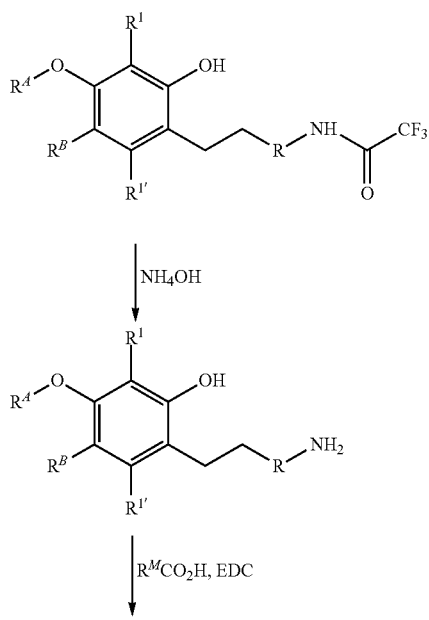

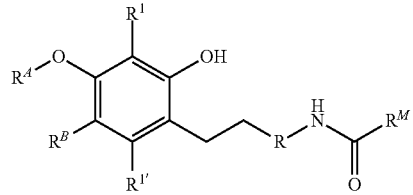

Typical electrophilic groups on macromolecules are carboxylic acid residues of amino acids in proteins or activated phosphoramidite reagents on immobilized oligonucleotide chains. In the enzyme mediated transamidation described above, the electrophile is a glutamine residue in a protein.

Reaction with Nucleophiles.

Reaction between a nucleophile-containing substrate or biological agent and an electrophilic derivative of the alkyl amine can also be used to form a covalent bond as illustrated below:

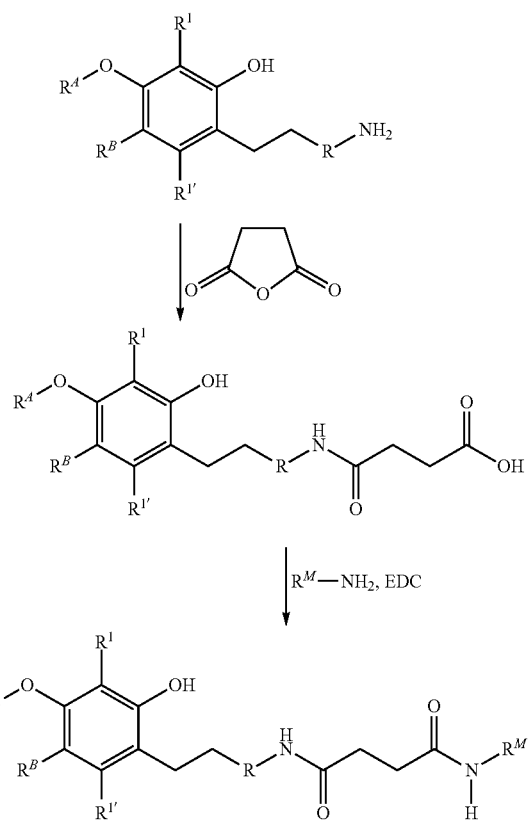

Typically, the nucleophiles are nitrogen nucleophiles (e.g., amines, hydrazines and the like) and the ligand ($R^M$) can be a biological compound (e.g., a nucleic acid, peptide, protein and the like) as illustrated below or an amine containing linking group that is used to attach the fluorescent molecule to, for example, a phosphoramidite group or a solid support as described by Glen Research (3'-aminomodifier C7 CPG) and illustrated below:

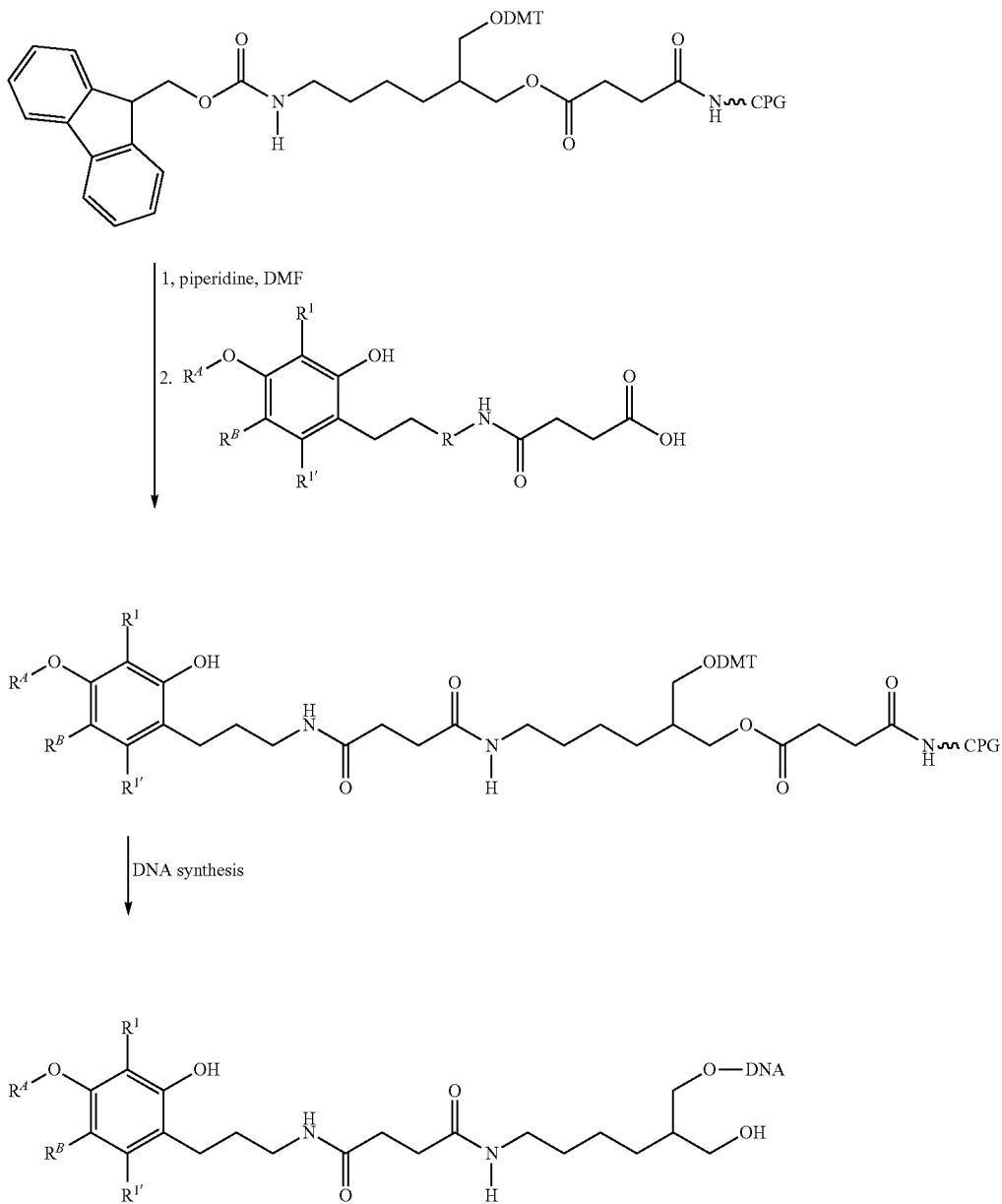

In view of the above, the present invention provides methods for labeling biological materials and methods for preparing phosphoramidite reagents or solid support reagents by reacting a fluorescent linked-alkyl amine dye derivative having a formula selected from compounds I to VI illustrated above with a suitable nucleophile to attach the fluorescent dye to a linking group, solid support, or biological material. In the above formulae, $R^1$ and $R^{1'}$ are each members independently selected from the group consisting of H, halogen, cyano, $CF_3$, $(C_1-C_8)$alkyl, $(C_1-C_8)$alkylthio, $(C_1-C_8)$alkoxy, aryl and heteroaryl; wherein the alkyl portions of any of $R^1$ or $R^{1'}$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^1$ or $R^{1'}$ are optionally substituted with from one to four substituents selected from the group consisting of halogen, cyano, carboxy, sulfo, hydroxy, amino, mono- or di$(C_3-C_6)$ alkylamino, $(C_1-C_6)$alkyl, $(C_1-C_6)$alkylthio and $(C_1-C_6)$ alkoxy. Additionally, the symbols $R^A$ and $R^B$ are combined to form a substituted or unsubstituted linked ring system having from 1 to 4 five- or six-membered rings; with the proviso that the compound has an emission wavelength of from 400 nm to 1200 nm, more preferably 400 nm to about 850 nm.

The specific linker arm structures illustrated are related to one method of synthesis of precursors using palladium catalyzed alkynylation as illustrated in Reaction Scheme 1 below.

The alkyne precursors can be partially hydrogenated to give alkenes or fully hydrogenated to give alkane linker arms. Friedyl Crafts acylation with phthalic anhydride gives the benzophenone intermediates of Type 1, 2, or 3. Further reaction of the benzophenones will be illustrated in the dye syntheses outlined below.

Reaction Scheme 1. General synthesis of Type 1, 2, and 3 substituted benzophenones.
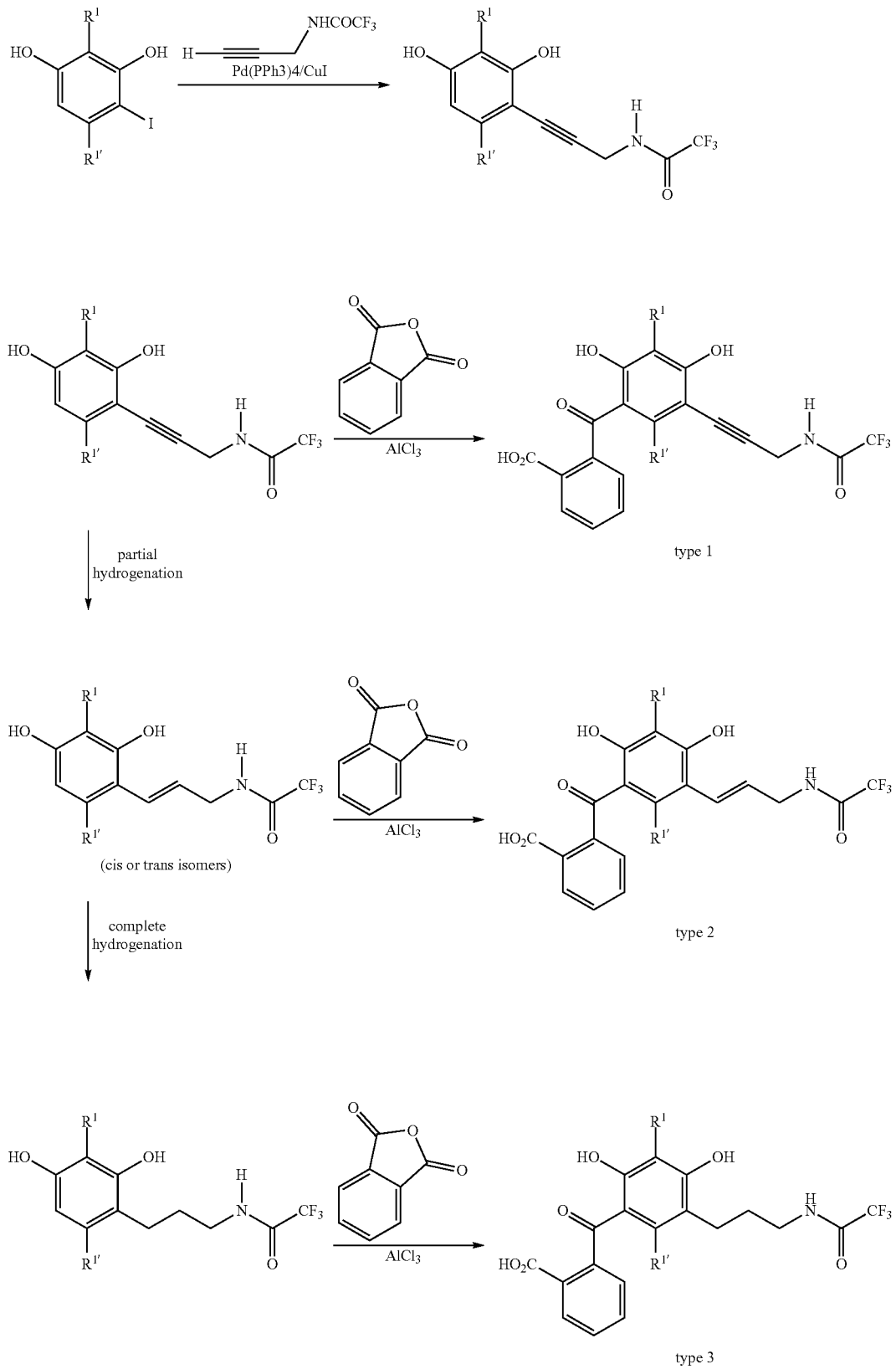

Alternatively, the palladium catalyzed alkynylation can be carried out as illustrated in Reaction Scheme 2 to give benzophenone intermediates of Type 4, 5, or 6:

Reaction Scheme 2. General synthesis of Type 4, 5, and 6 substituted benzophenones.

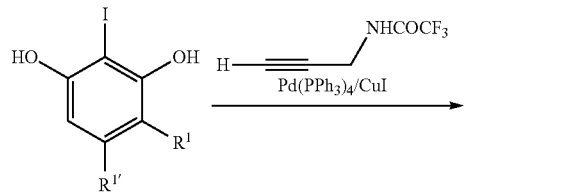

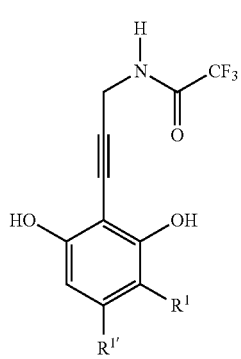

type 4

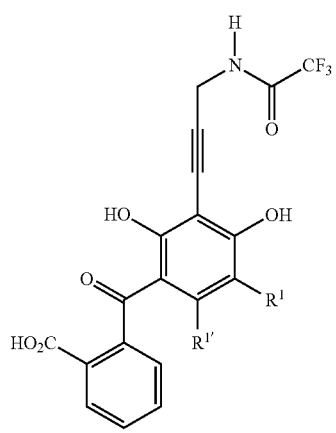

type 5

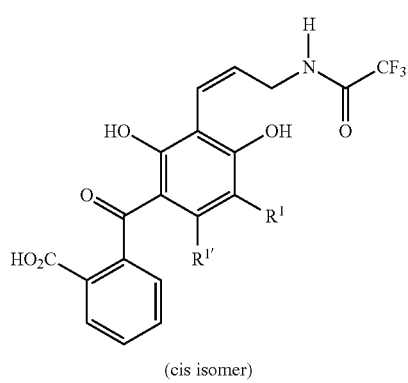

(cis isomer)

type 6

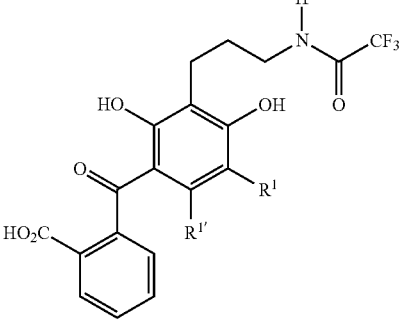

As illustrated in Reaction Schemes 1 and 2, the coupling of the halo-resorcinol and the alkyne introduces a C3-nitrogen containing group to the resorcinol core. The C3-nitrogen containing group ultimately becomes the linker arm (e.g., —$CH_2CH_2CH_2NH_2$) in the fluorescent dye compounds of the invention.

In one aspect, the invention provides alkyne compounds having the formula

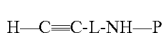

H—C≡C-L-NH—P wherein L is a linker moiety intermediate the alkyne group and the nitrogen atom, and wherein P is a nitrogen protecting group that is ultimately cleaved to provide an amino group (—$NH_2$), which can be further elaborated as described below.

Linker moiety L serves as a spacer between the alkyne group and the nitrogen atom. Linker moiety L has a length not exceeding the length of a normal alkyl chain of 25 carbons. Suitable linker moieties L include from one to about fifty (50) atoms selected from carbon, nitrogen, oxygen, hydrogen, and halogen. Representative L groups include alkylene groups (e.g., —$(CH_2)_n$—, where n is 1-12), phenylene groups (e.g., o-, m-, and p-$C_6H_4$—), and alkylene oxide groups (e.g., ethylene oxide, —$(CH_2CH_2O)_m$—, where m is 1-5). In one embodiment, L is —$(CH_2)$—.

Representative P groups include N-protecting groups known in the art suitable for protecting primary amine groups. Suitable N-protecting groups are described in T. W. Greene and P. G. Wuts, PROTECTIVE GROUPS IN ORGANIC CHEMISTRY, (Wiley, 2nd ed. 1991), expressly incorporated herein by reference in its entirety, In one embodiment, P is C(=O)$CF_3$).

In one embodiment, the alkyne is H—C≡C—$CH_2$—NH—C(=O)$CF_3$ (i.e., L is $CH_2$ and P is C(=O)$CF_3$).

As noted above, the alkyne compounds of the invention are useful for making the fluorescent dye compounds of the invention. In the fluorescent dye compounds of the invention, the linker arm is derived from the alkyne as illustrated in Reaction Schemes 1 and 2. Fluorescent dye compounds of the invention are described in detail below. In one embodiment, the linker arm is —$(CH_2)_3NH_2$ (which may exist in salt form depending on conditions).

In certain embodiments of the invention, the fluorescent dye compounds of the invention are functionalized to provide labeling agents. In these embodiments, the fluorescent dye compound's linker arm is functionalized by reaction of the linker arm's amino group. Suitable functionalization provides functionalized fluorescent dye compounds that are effective for reaction with a variety of materials including biomolecules (e.g., oligonucleotides, proteins, peptides).

In another aspect, the invention provides labeling agents having the formula

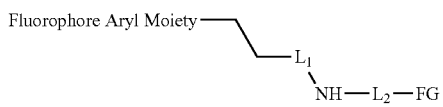

wherein the Fluorophore Aryl Moiety refers to the fluorescent core of the fluorescent dye compounds of the invention to which is attached the functionalized linker arm (i.e., —$CH_2CH_2$-$L_1$-NH-$L_2$-FG), wherein $L_1$ is a linker moiety intermediate the methylene group and the amine group ($L_1$ is the same as L in the alkyne compounds described above), wherein $L_2$ is a linker moiety intermediate the amine group and the functional group (FG), and wherein FG is a functional group reactive toward and capable of covalently coupling the fluorescent dye compound to a suitably reactive material.

Representative $L_1$ groups include the L groups described above for the alkyne.

Linker moiety $L_2$ serves as a spacer between the amine group and the functional group (FG). Linker moiety $L_2$ has a length not exceeding the length of a normal alkyl chain of 25 carbons. Suitable linker moieties $L_2$ include from one to about fifty (50) atoms selected from carbon, nitrogen, oxygen, hydrogen, and halogen. Representative $L_2$ groups include alkylene groups (e.g., —$(CH_1)_n$—, where n is 1-12), phenylene groups (e.g., o-, m-, and p-$C_6H_4$—), and alkylene oxide groups (e.g., ethylene oxide, —$(CH_2CH_2O)_m$—, where m is 1-5). Other suitable $L_2$ groups include —C(=$A_1$)-$L_1$-, —C(=$A_1$)NH-$L_1$-, —C(=$A_1$)NH-$L_1$-NH—, wherein $A_1$ is selected from O and S, and $L_1$ is as described above. In one embodiment, $L_2$ is —C(=O)—$(CH_2)_n$—, where n is 2-6.

Representative FG groups include carboxylic acid groups, carboxylic acid active esters (e.g., N-hydroxysuccinimide esters), maleimide groups, reactive carbamate and thiocarbamate groups, and α-haloacetamide groups (—NH—C(=O)—$CH_2$—X). Other suitable functional groups include groups that are capable of coupling the cycloaddition (e.g., dienes and dienophiles to provide 4+2 cycloaddition products, and acetylenes and azides (click chemistry)). In one embodiment, FG is a carboxylic acid group (—$CO_2$H) or its active esters (e.g., N-hydroxysuccinimide ester).

Carboxylic acid groups and carboxylic acid active esters are reactive toward amino groups including the amino group of lysine residues in proteins and peptides, and primary amino groups introduced into oligonucleotide probes (—C(=O)—NH— linkage). Maleimide groups are reactive to sulfhydryl groups native to or introduced into protein, peptide, and oligonucleotides (—N[C(=O)$CH_2$CHC(=O)]—S— linkages). Reactive carbamate and thiocarbamate groups are reactive toward amino groups to provide urea (—NH—C(=O)—NH—) and thiourea (—NH—C(=S)—NH—) linkages. α-Haloacetamide groups are reactive toward thiol groups to provide —NH—C(=O)—$CH_2$—S— linkages. Functional groups capable of conjugation through cycloaddition include dienes (e.g., furans) and dienophiles (e.g., alkenes and alkynes) that react to form 4+2 cycloaddition linkages. The linker arm can be modified to include either a diene or dienophile reactive toward a dienophile and diene, respectively, native to or incorporated into the complementary reactive material (e.g., biomolecule). Click chemistry can also be utilized for conjugation. The linker arm can be modified to include either a suitable acetylene (e.g., H—C≡C—R) or azide (e.g., R'—N=$N^+$=$N^-$) reactive toward an azide or acetylene, respectively, native to or incorporated into the complementary reactive material (e.g., biomolecule).

One of skill in the art will appreciate that the alkyl amine methodology (e.g., the synthesis of electrophilic or nucleophilic derivatives of alkyl amine dyes) described herein can be applied to essentially any dye having available valence sites for the alkyl amine linker arm.

While the present invention finds broad application to a number of fluorescent dyes, certain groups of dyes are preferred and are outlined below.

It will be appreciated that the compounds of the invention (e.g., general formulae (I), (II), (III), and (IV), and formulae Ia, Ib, IIa, IIb, IIIa, and IIIb) will be present in isomeric or tautomeric forms (e.g., Spiro or open ring forms) and, depending on their environment, acid/base and salt forms. When the tautomeric form has a hydroxy (or amine) group positioned, protected forms are also within the scope of the invention (e.g., protected hydroxy group or a protected amine group.

A. Xanthenes (Fluoresceins and Rhodols)

In one embodiment, the present invention provides xanthene linked-alkyl amine dyes having formulae Ia and Ib:

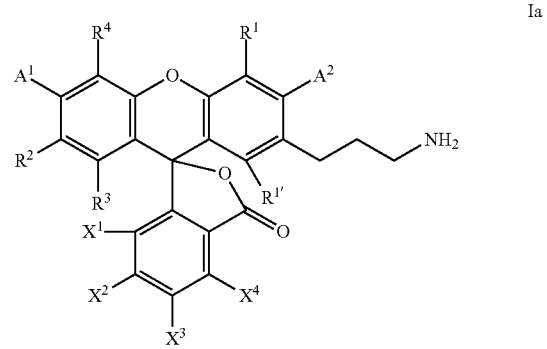

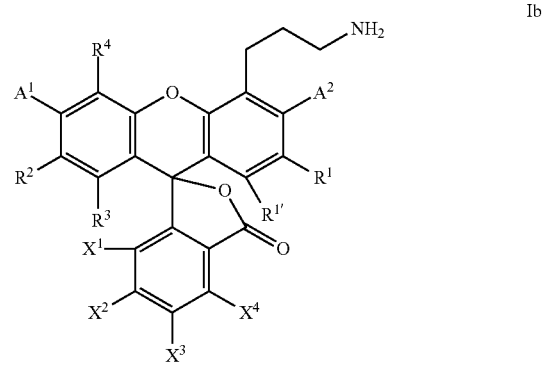

Formulae Ia and Ib: Xanthenes.

The propylamine linker shown can have any of the 6 structures shown above in Schemes 1 and 2.

For these xanthenes, $A^1$ and $A^2$ are independently selected from hydroxy, amino, mono- and dialkyl amino, protected hydroxy, protected amino, protected mono- and dialkyl amino, or when $A^1$ or $A^2$ is amino, mono- and dialkyl amino, $A^1$ and/or $A^2$ taken together with $R^2$ and/or $R^4$ (for $A^1$) or with $R^1$ (for $A^2$) and the atoms to which they are attached form a 5- or 6-membered nitrogen-containing ring.

$R^{1'}$, $R^1$, $R^2$, $R^3$, and $R^4$ are each independently selected from the group consisting of hydrogen, halogen, cyano, trifluoromethyl, ($C_1$-$C_8$)alkyl, ($C_1$-$C_8$)alkylthio and ($C_1$-$C_8$) alkoxy, aryl, and heteroaryl; $X^1$, $X^2$, $X^3$, and $X^4$ are each independently selected from the group consisting of hydrogen, halogen, cyano, trifluoromethyl, ($C_1$-$C_8$)alkyl, ($C_1$-$C_8$) alkoxy, ($C_1$-$C_8$)alkylthio, ($C_2$-$C_8$)alkenyl, ($C_2$-$C_8$)alkynyl, aryl, aryl($C_1$-$C_4$)alkyl, heteroaryl, $SO_3H$ and $CO_2H$; wherein the alkyl portions of any of $R^{1'}$ and $R^1$-$R^4$ and $X^1$-$X^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^{1'}$ and $R^1$-$R^4$ and $X^1$-$X^4$ are optionally substituted with from one to four substituents selected from the group consisting of halogen, cyano, carboxy, sulfo, hydroxy, amino, mono- or di($C_1$-$C_6$)alkylamino, ($C_1$-$C_6$)alkyl, ($C_1$-$C_6$)alkylthio and ($C_1$-$C_6$)alkoxy.

Further preferred are those compounds of formulae Ia and Ib wherein $A^1$ or $A^2$ is hydroxy or a protected hydroxy. Representative protecting groups are acyl groups derived from ($C_2$-$C_{20}$)alkanoic acids (e.g., acetyl, propionyl, pivaloyl, isobutyryl, and the like). Still further preferred are those compounds having a formula above in which $R^{1'}$ and $R^1$-$R^4$ and $X^1$-$X^4$ are independently selected from H, halogen, $CF_3$ and cyano. The linked-alkyl amine fluorescein dyes of the present invention can generally be prepared according to the scheme below, in which a suitably substituted resorcinol (i) is reacted with a substituted benzophenone (ii), then lactonized to produce the desired compounds (iii). Certain substituents are not included in the formula below. A more detailed reaction scheme and a table of particularly preferred alkyl amine dyes in this group are provided in the section entitled "General Synthesis of Alkyl Amine Dyes."

Reaction Scheme 3. General synthesis of substituted fluroescein dyes

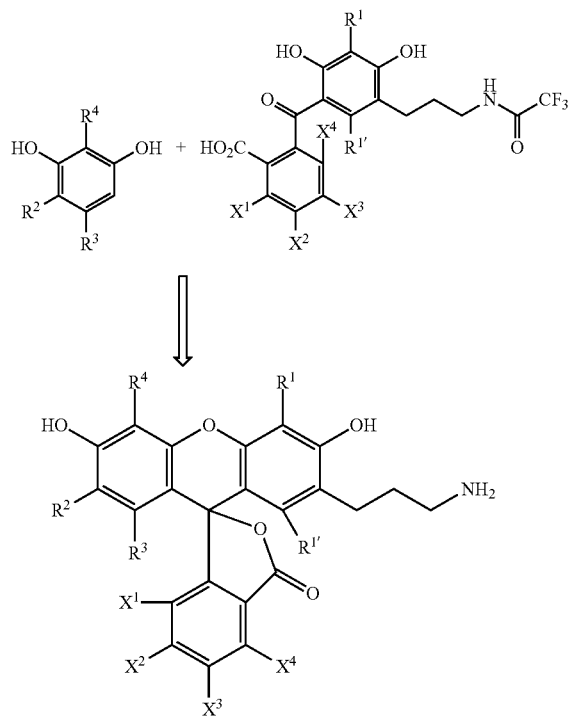

B. Benzo[a]xanthenes

In another embodiment, the present invention provides benzo[a]xanthene linked-alkyl amine dyes having formulae IIa and IIb:

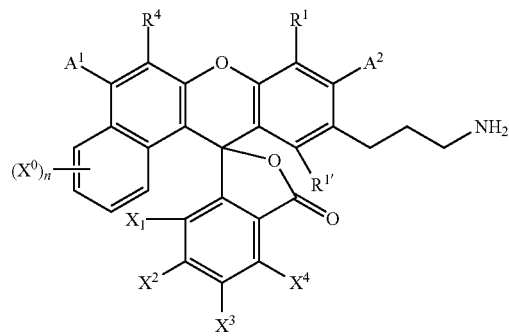

IIa

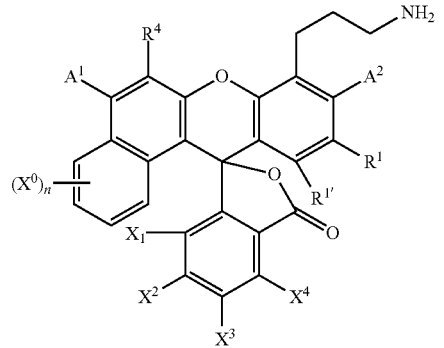

IIb

Formulae IIa and IIb: Benzo[a]xanthenes.

Note that the propylamine linker shown can have any of the 6 structures shown in Schemes 1 and 2.

For the benzo[a]xanthenes, $A^1$ and $A^2$ are independently selected from hydroxy, amino, mono- and dialkyl amino, protected hydroxy, protected amino, protected mono- and dialkyl amino, or when $A^1$ or $A^2$ is amino, mono- and dialkyl amino, $A^1$ and/or $A^2$ taken together with $R^4$ (for $A^1$) or with $R^1$ (for $A^2$) and the atoms to which they are attached form a 5- or 6-membered nitrogen-containing ring.

$R^{1'}$, $R^1$, $R^4$, $X^0$, and $X^1$-$X^4$ are the same as $R^{1'}$ and $R^1$-$R^4$ and $X^1$-$X^4$ described above for formulae Ia and Ib, and n is 1, 2, 3, or 4.

Preferred are those compounds of wherein $A^1$ or $A^2$ is hydroxy or a protected hydroxy. Preferred protecting groups are acyl groups derived from ($C_2$-$C_{20}$)alkanoic acids (e.g., acetyl, propionyl, pivaloyl, isobutyryl, and the like). More preferably, $R^{1'}$ and $R^1$ through $R^4$ and $X^1$ through $X^4$ are independently selected from H, halogen, $CF_3$ and cyano; and each $X^0$ is H, halogen, $CF_3$ or cyano. In other embodiments, two of $X^1$ through $X^4$ are combined to form a six-membered aromatic ring. In other embodiments, in the compounds of IIa and IIb, each of $X^1$ through $X^4$ is H. Most preferred are those embodiments in which $A^1$ or $A^2$ is hydroxy or protected hydroxy; each of $X^1$ through $X^4$ is H; each of $X^1$ through $X^4$ is H, F, or Cl; and $R^1$, $R^{1'}$, and $R^4$ are each independently selected from H, F, Cl, CN and $CF_3$.

In general, these compounds can be prepared according to the procedure in Reaction Scheme 4.

Reaction Scheme 4. General synthesis of substituted benzo[a]xanthene dyes.

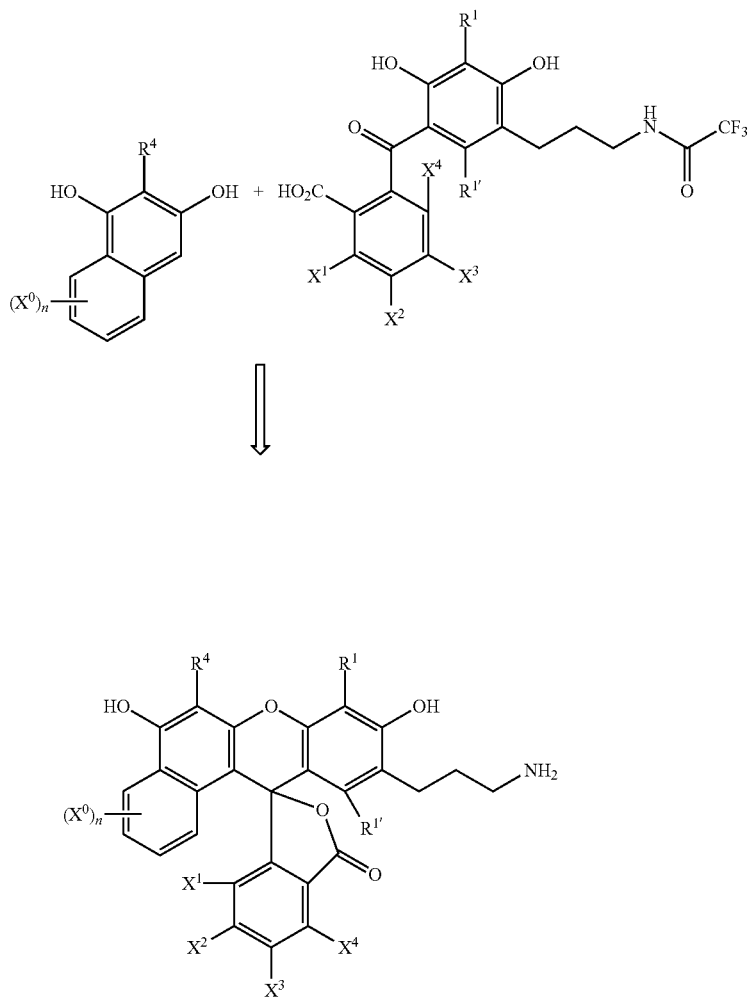

C. Benzo[c]xanthenes

In a further embodiment, the present invention provides benzo[c]xanthene linked-alkyl amine dyes having formulae IIIa and IIIb:

IIIa

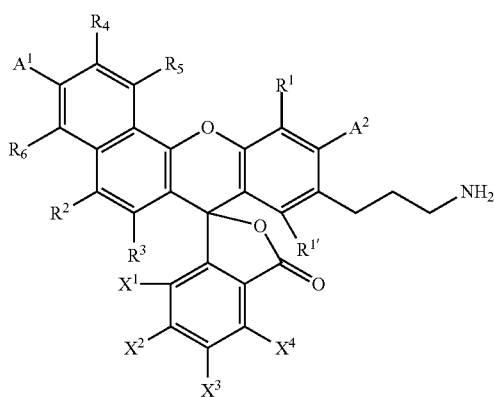

IIIb

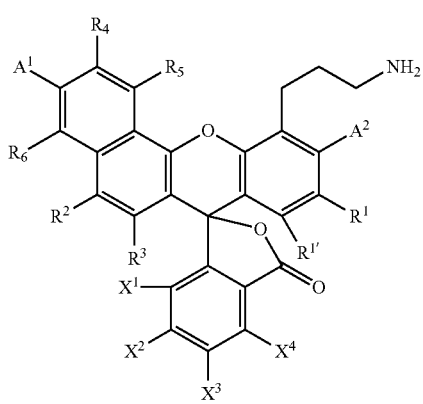

Formulae IIIa and IIIb: Benzo[c]xanthenes.

Note that the propylamine linker shown can have any of the 6 structures shown in Schemes 1 and 2.

For the benzo[c]xanthenes, $A^1$ and $A^2$ are independently selected from hydroxy, amino, mono- and dialkyl amino, protected hydroxy, protected amino, protected mono- and dialkyl amino, or when $A^1$ or $A^2$ is amino, mono- and dialkyl amino, $A^1$ and/or $A^2$ taken together with $R^4$ or $R^6$ (for $A^1$) or with $R^1$ (for $A^2$) and the atoms to which they are attached form a 5- or 6-membered nitrogen-containing ring.

$R^{1'}$, $R^1$-$R^6$, and $X^1$-$X^4$ are selected from the same substituents as $R^{1'}$ and $R^1$-$R^4$ and $X^1$-$X^4$ described above for formulae Ia and Ib.

In certain embodiments, $A^1$ or $A^2$ is hydroxy or a protected hydroxy. Preferred protecting groups are acyl groups derived from ($C_2$-$C_{20}$)alkanoic acids (e.g.: acetyl, propionyl, pivaloyl, isobutyryl, and the like). In other embodiments, $R^{1'}$ and $R^1$-$R^4$ and $X^1$-$X^4$ are independently selected from H, halogen, $CF_3$ and cyano. In other embodiments, two of $X^1$-$X^4$ are combined to form a six-membered aromatic or heteroaromatic ring. In other embodiments, in the compounds of IIIa and IIIb, each of $X^1$-$X^4$ is H.

In one embodiment, $R^4$ is a halogen (e.g., chloro). In another embodiment, $R^6$ is a halogen (e.g., chloro). In a further embodiment, $R^4$ and $R^6$ are halogens (e.g., chloro).

In general, these compounds can be prepared according to the procedure in Reaction Scheme 5.

Synthesis of Alkyl Amine Dyes

Many of the linked-alkyl amine dyes can be prepared from common intermediate that are readily available to one of skill in the art. Two groups of particularly useful intermediates are the benzophenone derivatives of Types 1-6 shown above in Reaction Schemes 1 and 2. The synthetic approaches herein are based on utilizing the versatile substituted alkyl amine benzophenones in conjunction with known synthetic routes for dye assembly. The application of the intermediates is not limited to the classes described below, but finds broad application to any resorcinol based dye chemistry. Moreover, the intermediates described above can be prepared using a variety of other art-recognized methods.

Xanthene Dye Alkyl Amines.

Synthesis of asymmetrical xanthene dyes are accomplished in two stages. At the first stage benzophenones are prepared by Friedel-Crafts acylation of resorcinol analogs with phthalic anhydrides in the presence of aluminum trichloride. At the second stage ketones are condensed with resorcinols using either methanesulfonic or trifluoroacetic (plus catalytic methanesulfonic acid) acid as a solvent.

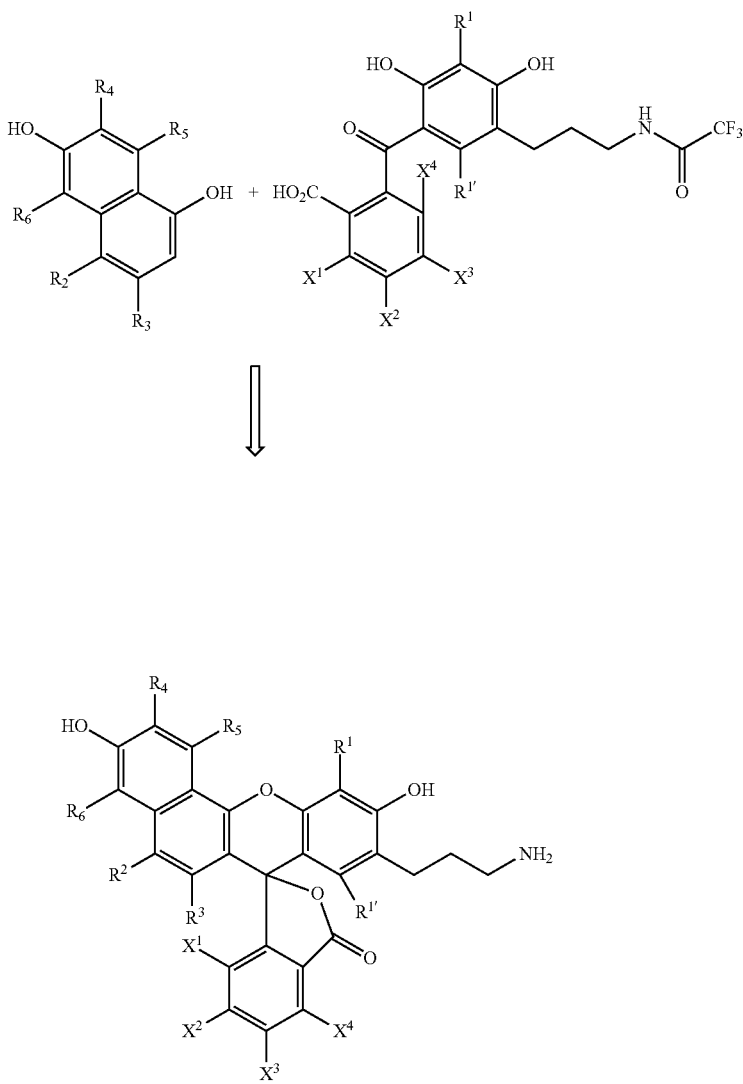

Reaction Scheme 5. General synthesis of substituted benzo[c]xanthene dyes.

Reaction Scheme 6. Synthesis of a yellow-emitting fluorescein analog with TFA protected alkyl amine linker. Expected Absorbance = 531 nm, expected Emission = 549 nm (18 nm Stokes shift)

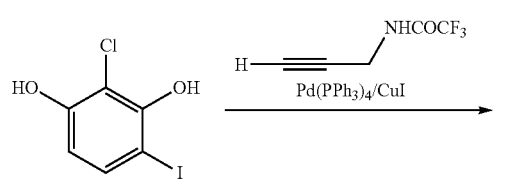

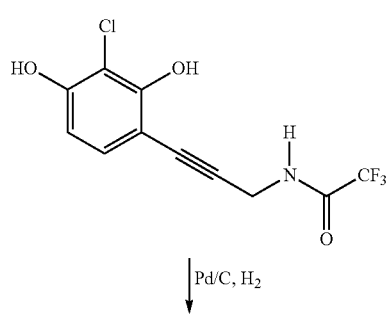

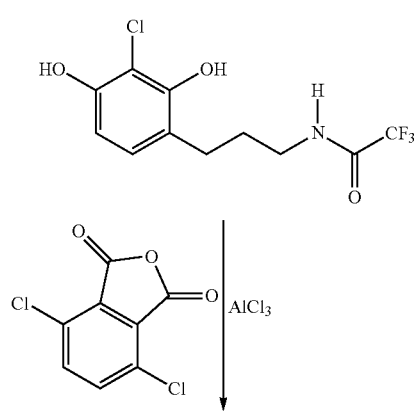

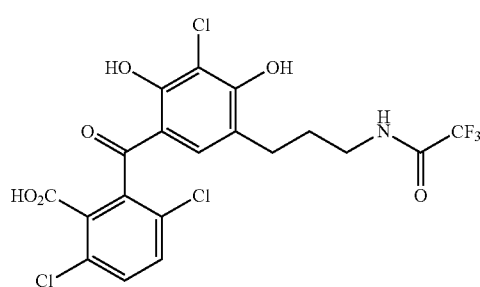

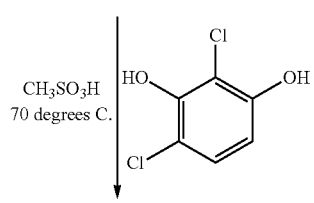

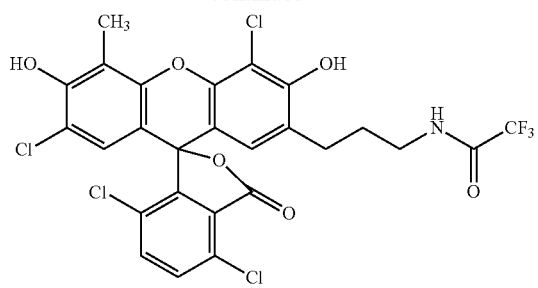

Benzo[a]xanthene Dye Alkyl Amines.

These compounds are synthesized analogously to xanthene dyes (Reaction Scheme 6) using condensation of benzophenones with 1,3-dihydroxynaphthalenes. In the example shown in Scheme 7, removal of the TFA protecting group and succinylation of the alkyl amine linker is executed at the benzophenone stage.

Reaction Scheme 7. Synthesis of an orange-emitting benzo[a]xanthene analog with succinylated alkyl amine linker. Expected Absorbance = 538 nm, expected Emission = 565 nm (27 nm Stokes shitf).

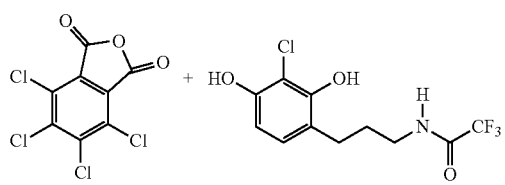

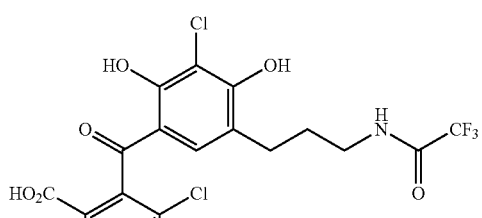

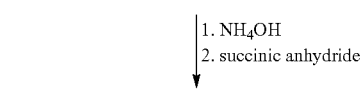

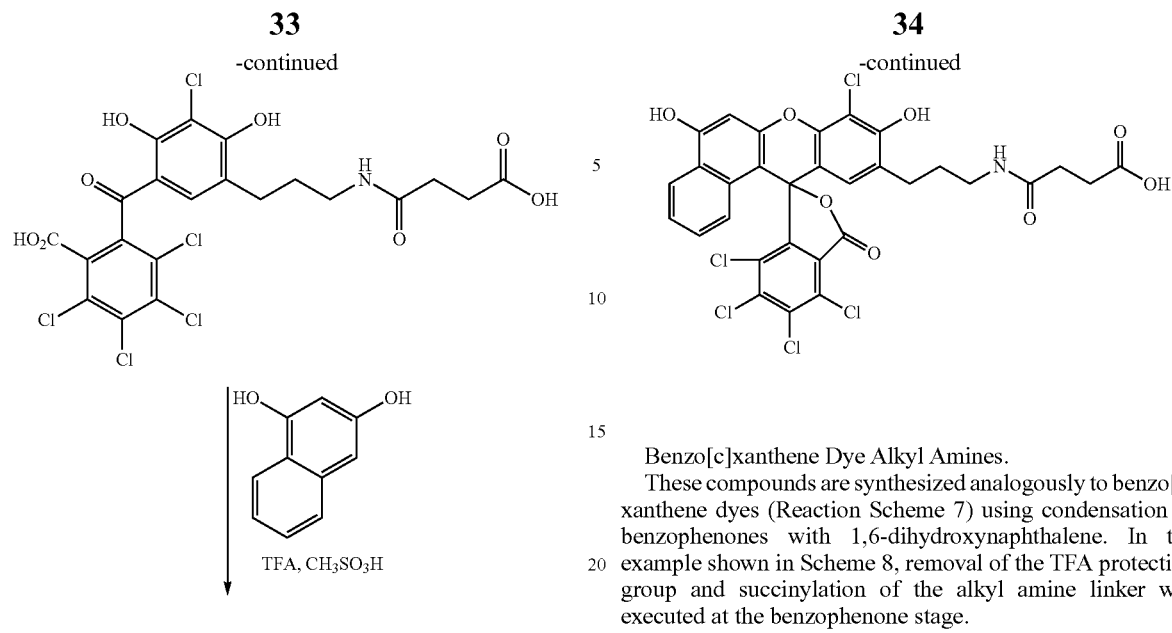

Benzo[c]xanthene Dye Alkyl Amines.

These compounds are synthesized analogously to benzo[a]xanthene dyes (Reaction Scheme 7) using condensation of benzophenones with 1,6-dihydroxynaphthalene. In the example shown in Scheme 8, removal of the TFA protecting group and succinylation of the alkyl amine linker was executed at the benzophenone stage.

Reaction Scheme 8. Synthesis of a red-emitting benzo[c]xanthene analog with succinylated alkyl maine linker (BCSI-3). Absorbance = 535 nm, Emission = 610 nm (75 nm Stokes shift).

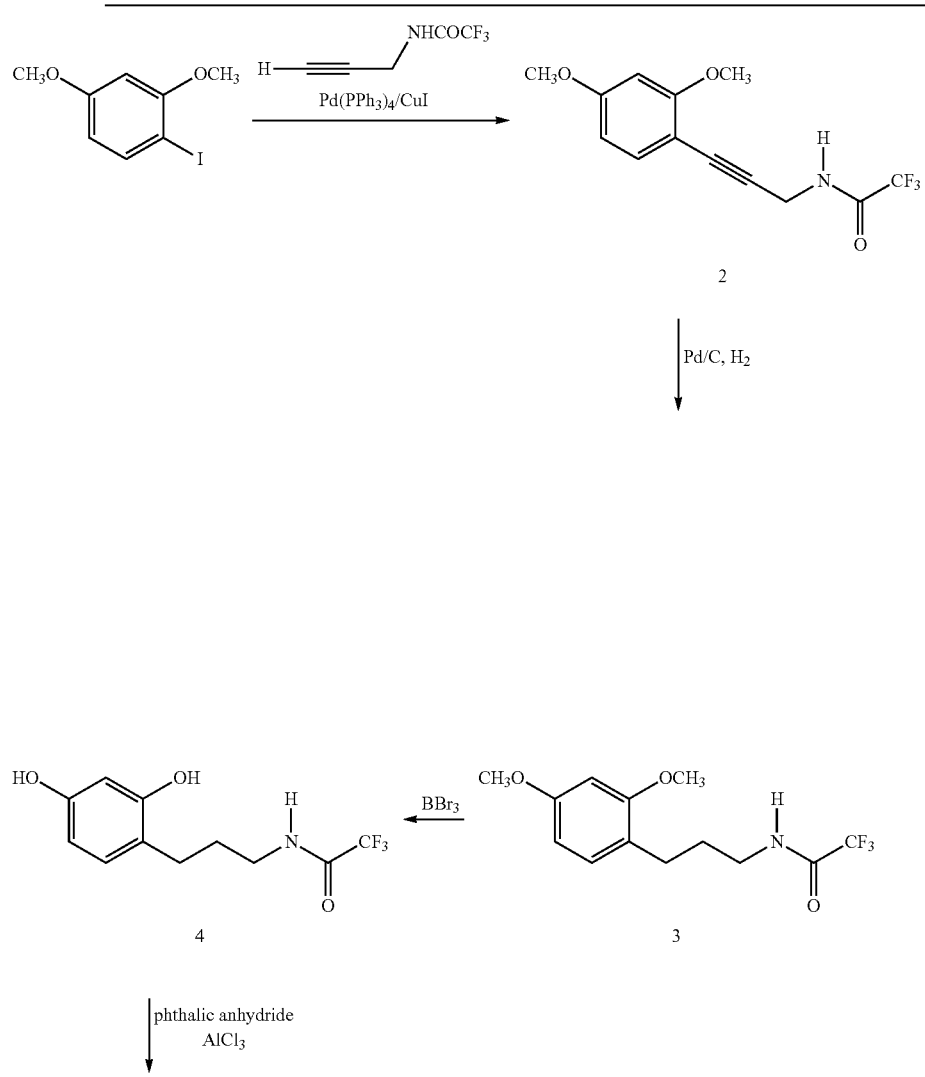

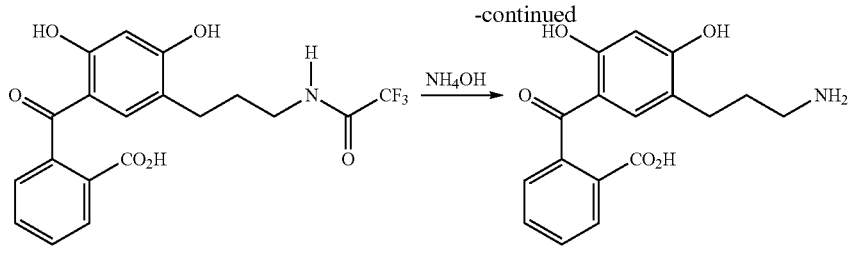

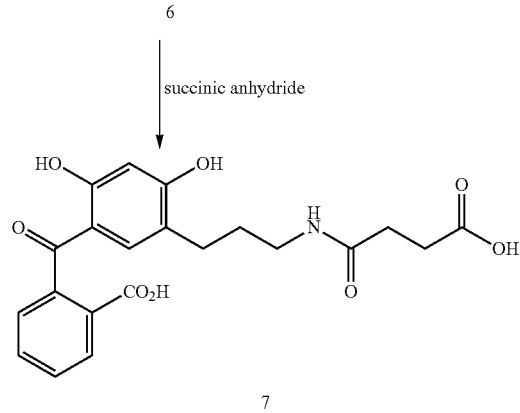

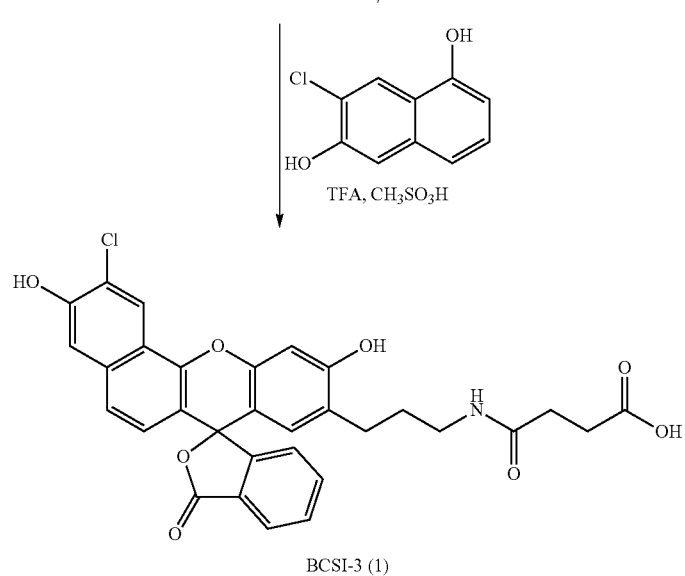

BCSI-3 (1)

Benzo[c]xanthene Linker Compounds

In another embodiment, the fluorescent species is a benzo[c]xanthene linker compound.

Representative benzo[c]xanthene linker compounds include compounds of formulae (I), (II), (III), and (IV), their salts, active esters, acid/base forms, and tautomers.

Each of the benzo[c]xanthene linker compounds of formulae (I), (II), (III), and (IV) includes a linker arm.

For the alkyl amine compounds of the invention (formulae (III) and (IV)), the term "linker arm" refers to a moiety having the formula

—CH₂CH₂-L-NH₂ wherein L is a linker moiety intermediate the methylene group and the amino nitrogen atom. Linker moiety L serves as a spacer between the alkyne group and the nitrogen atom. Linker moiety L has a length not exceeding the length of a normal alkyl chain of 25 carbons. Suitable linker moieties L include from one to about fifty (50) atoms selected from carbon, nitrogen, oxygen, hydrogen, and halogen. Representative L groups include alkylene groups (e.g., —(CH$_2$)$_n$—, where n is 1-12), phenylene groups (e.g., o-, m-, and p-C$_6$H$_4$—), and alkylene oxide groups (e.g., ethylene oxide, —(CH$_2$CH$_2$O)$_m$—, where m is 1-5). In one embodiment, L is CH$_2$. In one embodiment, the linker arm is —(CH$_2$)$_3$NH$_2$. It will be appreciated that the amino group of the linker arm may exist in salt form depending on the environment.

As noted above, in certain aspects of the invention, the fluorescent dye compounds of the invention are functionalized to provide labeling agents. In these embodiments, the fluorescent dye compound's linker arm is functionalized by reaction of the linker arm's amino group. Suitable functionalization provides functionalized fluorescent dye compounds that are effective for reaction with a variety of materials including biomolecules (e.g., oligonucleotides, proteins, peptides).

For the fluorescent compounds of the invention suitable as labeling agents (formulae (III) and (IV)), the term "linker arm" refers to a group of atoms that includes a functional group capable of reaction with a site on an oligonucleotide, protein, peptide, other biomolecule or macromolecule, or solid surface. In certain embodiments, the linker arm has the formula:

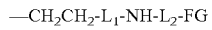

wherein $L_1$ is a linker moiety intermediate the adjacent methylene group ($CH_2$) and the amine group (NH), wherein $L_2$ is a linker moiety intermediate the amine group (NH) and the functional group (FG), and wherein FG is a functional group reactive toward and capable of covalently coupling the fluorescent dye compound to a suitably reactive material.

Linker moiety $L_1$ serves as a spacer between the methylene group and the nitrogen atom. Linker moiety $L_1$ has a length not exceeding the length of a normal alkyl chain of 25 carbons. Suitable linker moieties $L_1$ include from one to about fifty (50) atoms selected from carbon, nitrogen, oxygen, hydrogen, and halogen. Representative $L_1$ groups include alkylene groups (e.g., —$(CH_2)_n$—, where n is 1-12), phenylene groups (e.g., o-, m-, and p-$C_6H_4$—), and alkylene oxide groups (e.g., ethylene oxide, —$(CH_2CH_2O)_m$—, where m is 1-5). In one embodiment, $L_1$ is —$(CH_2)$—.

Linker moiety $L_2$ serves as a spacer between the amine group (NH) and the functional group (FG). Linker moiety $L_2$ has a length not exceeding the length of a normal alkyl chain of 25 carbons. Suitable linker moieties $L_2$ include from one to about fifty (50) atoms selected from carbon, nitrogen, oxygen, hydrogen, and halogen. Representative $L_2$ groups include alkylene groups (e.g., —$(CH_1)_n$—, where n is 1-12), phenylene groups (e.g., o-, m-, and p-$C_6H_4$—), and alkylene oxide groups (e.g., ethylene oxide, —$(CH_2CH_2O)_m$—, where m is 1-5). Other suitable $L_2$ groups include —$C(=A_1)$-$L_1$-, —$C(=A_1)NH$-$L_1$-, —$C(=A_1)NH$-$L_1$-$NH$—, wherein $A_1$ is selected from O and S, and $L_1$ is as described above. In one embodiment, $L_2$ is —$C(=O)$—$(CH_2)_n$—, where n is 2-6.

Representative FG groups include carboxylic acid groups, carboxylic acid active esters (e.g., N-hydroxysuccinimide esters), maleimide groups, reactive carbamate and thiocarbamate groups, and α-haloacetamide groups (—NH—C(=O)—$CH_2$—X). Other suitable functional groups include groups that are capable of coupling the cycloaddition (e.g., dienes and dienophiles to provide 4+2 cycloaddition products, and acetylenes and azides (click chemistry)). In one embodiment, FG is a carboxylic acid group (—$CO_2H$) or its active esters (e.g., N-hydroxysuccinimide ester).

Carboxylic acid groups and carboxylic acid active esters are reactive toward amino groups including the amino group of lysine residues in proteins and peptides, and primary amino groups introduced into oligonucleotide probes (—C(=O)—NH— linkage). Maleimide groups are reactive to sulfhydryl groups native to or introduced into protein, peptide, and oligonucleotides (—N[C(=O)$CH_2$CHC(=O)]—S— linkages). Reactive carbamate and thiocarbamate groups are reactive toward amino groups to provide urea (—NH—C(=O)—NH—) and thiourea (—NH—C(=S)—NH—) linkages. α-Haloacetamide groups are reactive toward thiol groups to provide —NH—C(=O)—$CH_2$—S— linkages. Functional groups capable of conjugation through cycloaddition include dienes (e.g., furans) and dienophiles (e.g., alkenes and alkynes) that react to form 4+2 cycloaddition linkages. The linker arm can be modified to include either a diene or dienophile reactive toward a dienophile and diene, respectively, native to or incorporated into the complementary reactive material (e.g., biomolecule). Click chemistry can also be utilized for conjugation. The linker arm can be modified to include either a suitable acetylene (e.g., H—C≡C—R) or azide (e.g., R'—N=N$^+$=N$^-$) reactive toward an azide or acetylene, respectively, native to or incorporated into the complementary reactive material (e.g., biomolecule).

In one embodiment, the linker arm has the formula:

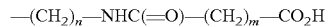

wherein n is an integer from 1 to 12 and m is an integer from 1 to 12. In certain embodiments, n is an integer from 1 to 4. In certain embodiments, m is an integer from 1 to 4. In one embodiment, n is 3 and m is 2.

The preparation of a representative fluorescent species, BCSI-3, is described in Example 1. FIG. 1 illustrates the synthesis of a representative 2-halo seminaphthofluorescein compound (BCSI-3).

Figure 2:
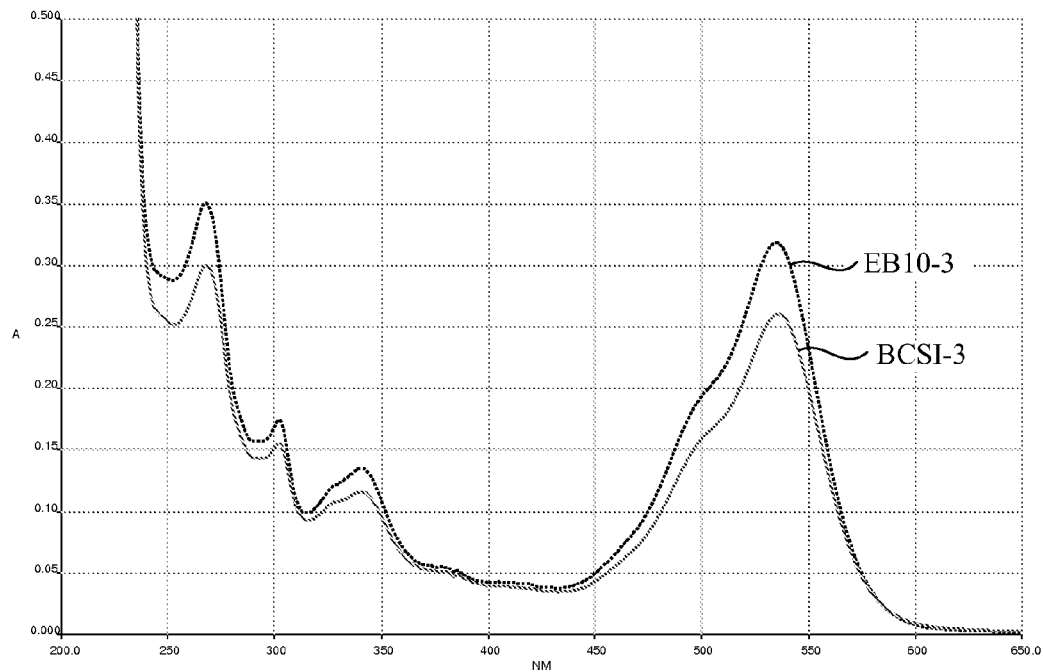
FIG. 2 compares the absorbance spectra of two representative fluorescent species (EBIO-3 and BCSI-3) at pH 9.5 (borate buffer).
Figure 3:
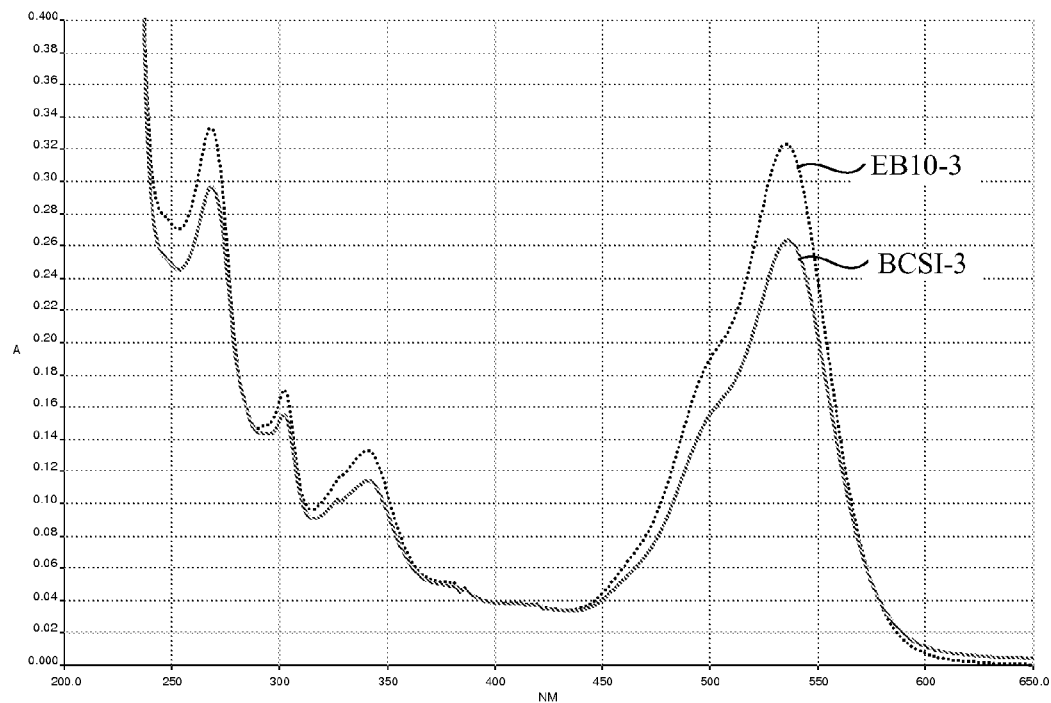
FIG. 3 compares the absorbance spectra of two representative fluorescent species (EBIO-3 and BCSI-3) at pH 7.4 (phosphate buffered saline).
Figure 4:
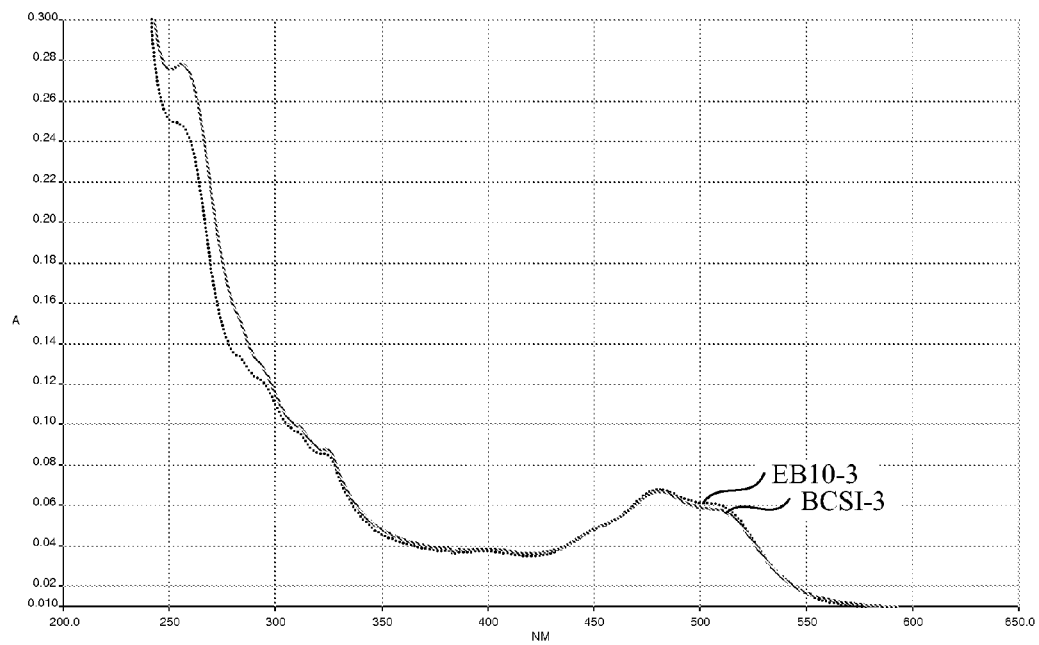
FIG. 4 compares the absorbance spectra of two representative fluorescent species (EBIO-3 and BCSI-3) at pH 4.5 (acetate buffer).

The absorbance spectra of two representative fluorescent species (EBIO-3 and BCSI-3) are compared in FIGS. 2-4. FIG. 2 compares the absorbance spectra of two representative fluorescent species (EBIO-3 and BCSI-3) at pH 9.5 (borate buffer). FIG. 3 compares the absorbance spectra of two representative fluorescent species (EBIO-3 and BCSI-3) at pH 7.4 (phosphate buffered saline). FIG. 4 compares the absorbance spectra of two representative fluorescent species (EBIO-3 and BCSI-3) at pH 4.5 (acetate buffer).

Figure 5:
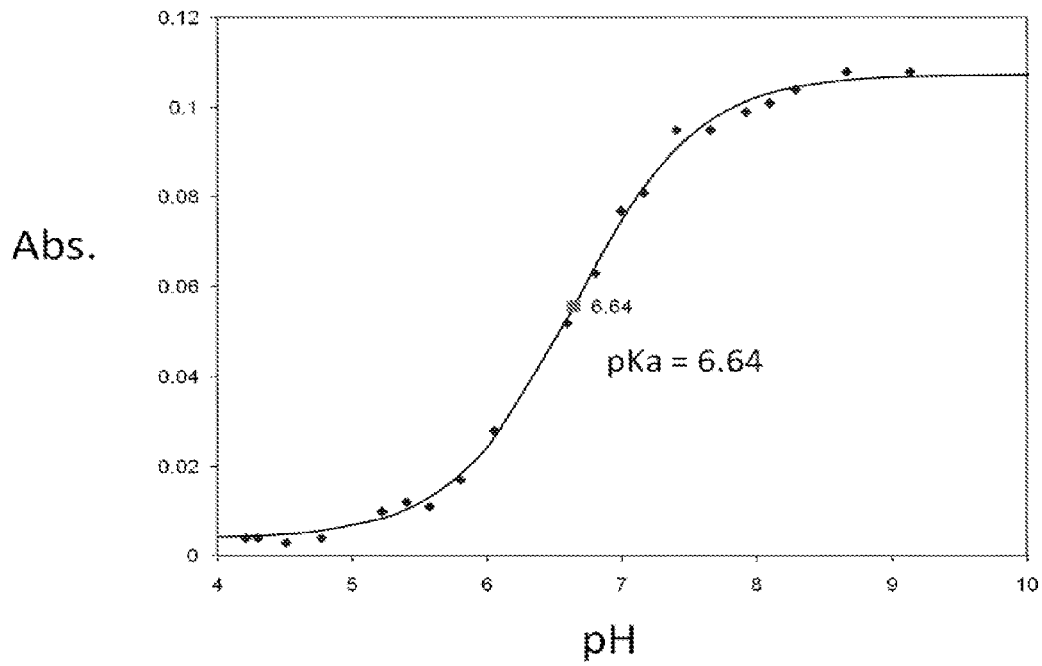
FIG. 5 illustrates the pKa determination of a representative fluorescent species (EBIO-3) by plotting peak absorbance (530 nm) as a function of pH.
Figure 6:
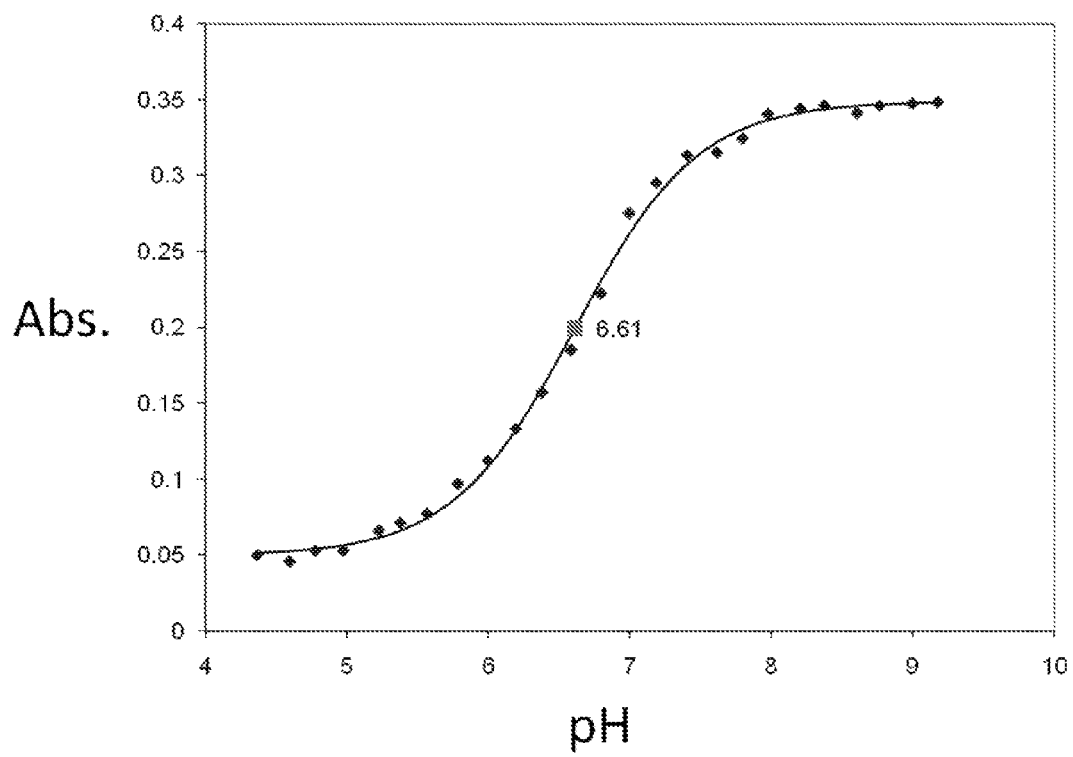
FIG. 6 illustrates the pKa determination of a representative fluorescent species (BCSI-3) by, plotting peak absorbance (530 nm) as a function of pH.

The pKa of the two representative fluorescent species (EBIO-3 and BCSI-3) are comparable. FIG. 5 illustrates the pKa determination of a representative fluorescent species (EBIO-3) by plotting peak absorbance (530 nm) as a function of pH. FIG. 6 illustrates the pKa determination of a representative fluorescent species (BCSI-3) by plotting peak absorbance (530 nm) as a function of pH.

Figure 7:
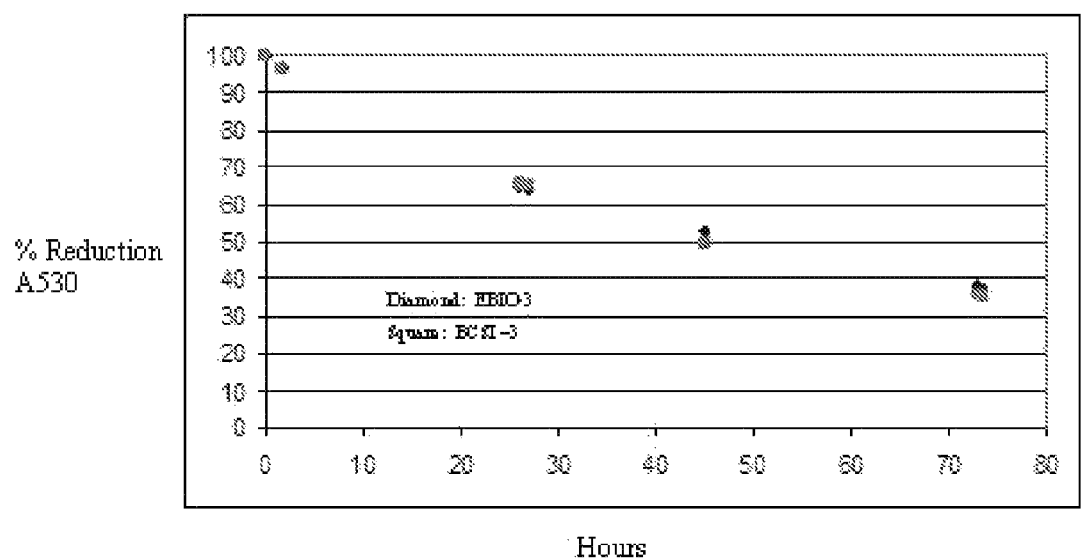
FIG. 7 compares the photodegradation of the two representative fluorescent species (EBIO-3 and BCSI-3) at pH 7.4 (phosphate buffered saline) by plotting percent reduction in absorbance at 530 nm as a function of exposure to light.

The photostability of the two representative fluorescent species (EBIO-3 and BCSI-3) are comparable. FIG. 7 compares the photodegradation of the two representative fluorescent species (EBIO-3 and BCSI-3) at pH 7.4 (phosphate buffered saline) by plotting percent reduction in absorbance at 530 nm as a function of exposure to light.

Figure 8:
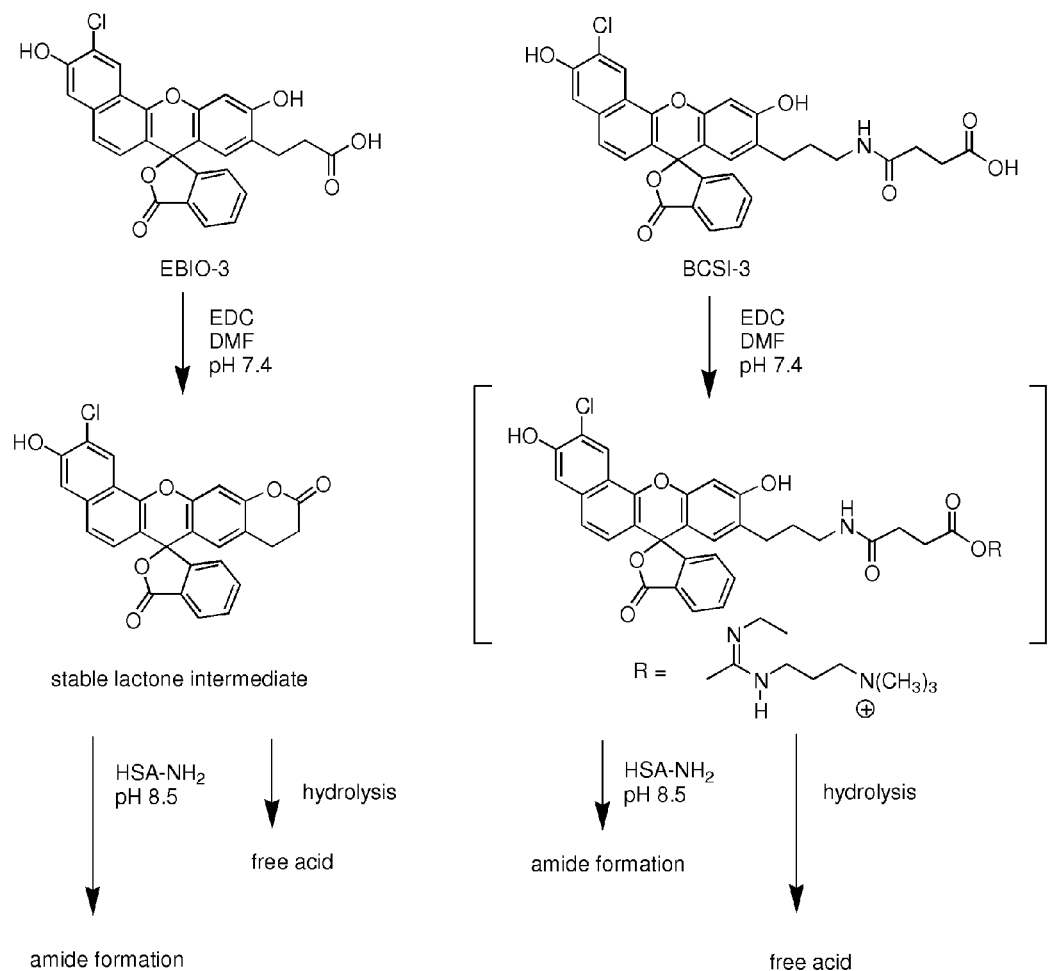
FIG. 8 is a schematic illustration comparing the preparation of two representative fluorophore-protein conjugates (EBIO-3/HSA and BCSI-3/HSA).

In one embodiment, the fluorophore-protein conjugate is a conjugate of a benzo[c]xanthene linker compound of formulae (I) or (II) and a protein. The preparation of a representative fluorophore-protein conjugate (BCSI-3/HSA) is described in Example 2. FIG. 8 is a schematic illustration comparing the preparation of two representative fluorophore-protein conjugates (EBIO-3/HSA and BCSI-3/HSA).

Figure 9:
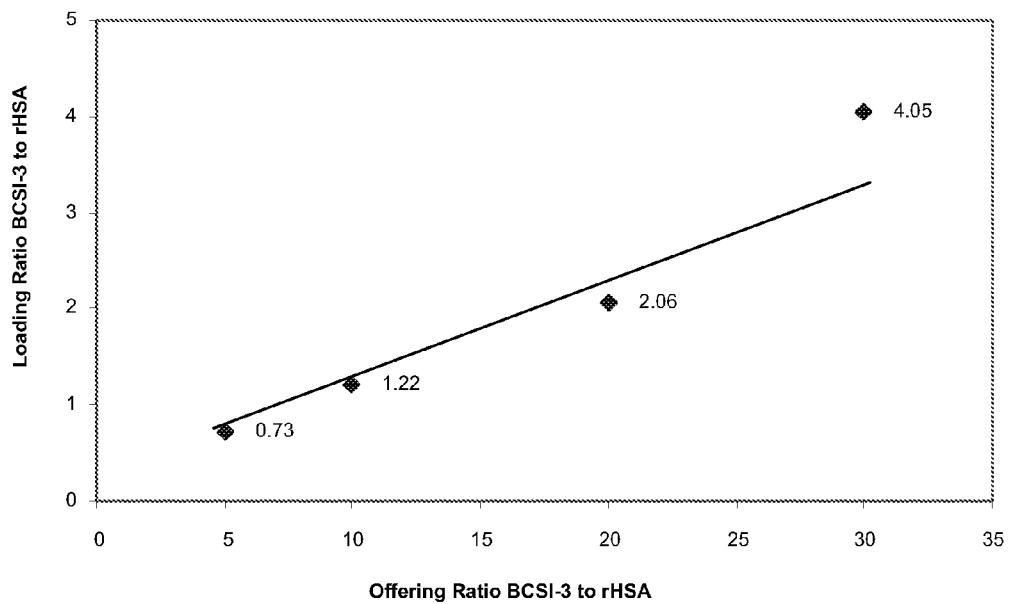
FIG. 9 is a graph illustrating loading ratio of a representative fluorescent species (BCSI-3) to a representative protein (rHSA) as a function of offering ratio (BCSI-3/rHSA).
Figure 10:
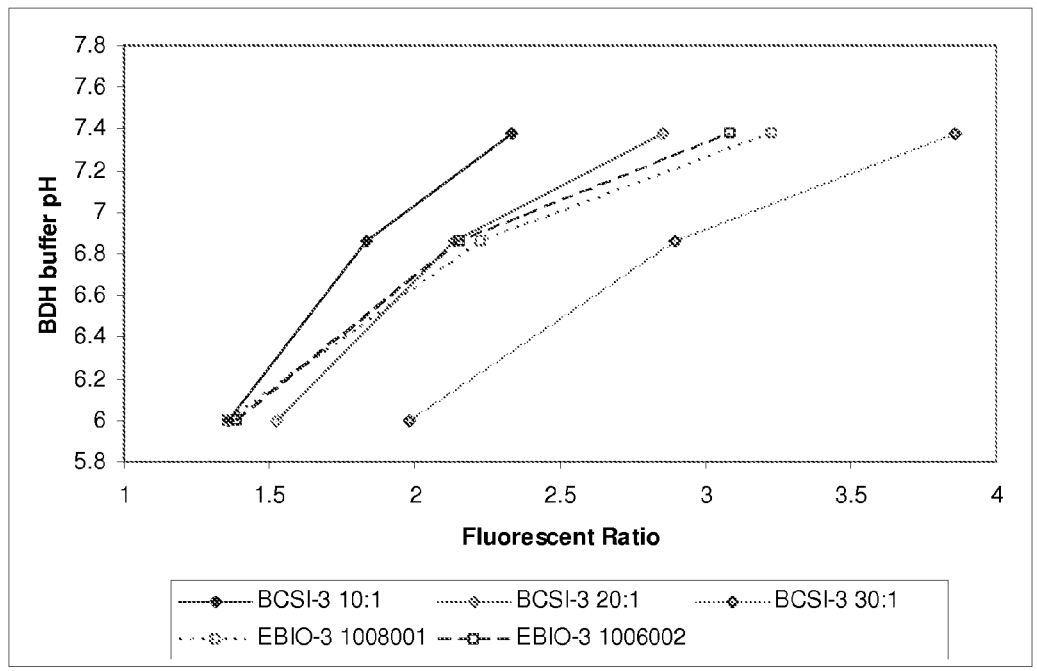
FIG. 10 compares fluorescent ratio signal as a function of test buffer pH for representative fluorophore-protein conjugates (EBIO-3/HSA and BCSI-3/HSA conjugates).

FIG. 9 is a graph illustrating loading ratio of a representative fluorescent species (BCSI-3) to a representative protein (rHSA) as a function of offering ratio (BCSI-3/rHSA). FIG. 10 compares fluorescent ratio signal as a function of test buffer pH for representative fluorophore-protein conjugates (EBIO-3/HSA and BCSI-3/HSA conjugates).

Figure 11:
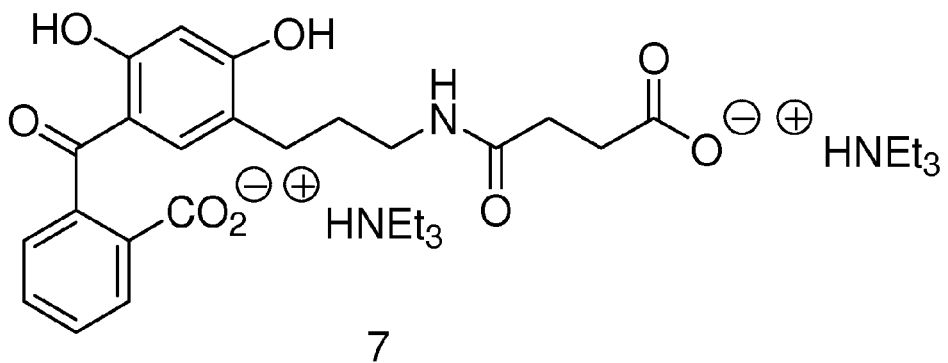
FIG. 11 illustrates the synthesis of a representative xanthene compound of the invention (GR dye).
Figure 11:
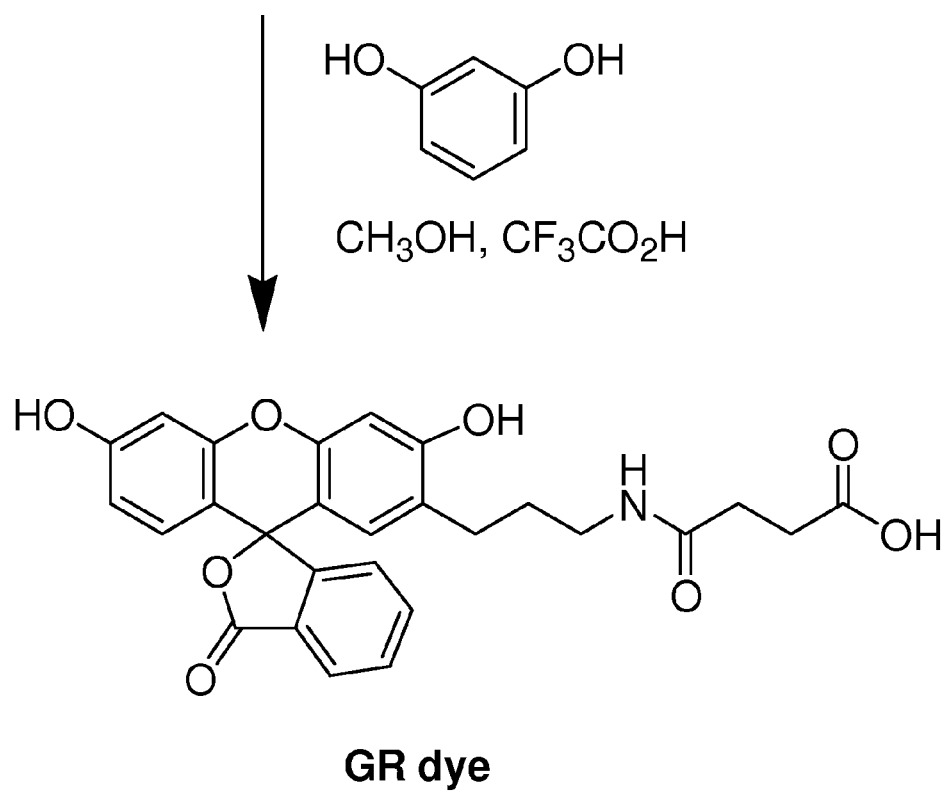

The preparation of a second representative fluorescent fluorescein species (GR dye) of the invention is described in Example 3. FIG. 11 illustrates the synthesis of the representative fluorescein compound.

Fluorescent Labels

In another aspect of the invention, fluorescently labeled compounds and conjugates are provided. The fluorescently labeled compounds and conjugates can be prepared from the compounds of the invention described herein (e.g., benzo[c]xanthene compounds of formulae (I) and (II), their salts, active ester, acid/base forms, and tautomers) and macromolecules including proteins, polypeptides, peptides, and nucleic acids. Fluorescently-labeled proteins (e.g., antibodies, antibody fragments, receptors, receptor fragments, enzyme substrates) and nucleic acids (e.g., fluorogenic nucleic acid probes derived from DNA, RNA) are conveniently prepared from the compounds of the invention, or their reactive derivatives, for use in molecular diagnostic assays.

The low pKa and large Stokes shift of the compounds provide a unique advantage for use in assays that function in the pH range above 7.5.

Nucleic Acid Labeling Reagents

In another aspect of the invention, nucleic acid labeling reagents are provided. Labeled nucleic acid probes (e.g., hydridization probes and hydrolysis probes) can be prepared using the compounds of the invention described herein (e.g., benzo[c]xanthene compounds of formulae (I) and (II), their salts, active ester, acid/base forms, and tautomers) in the form of activated esters, phosphoramidites, and solid supports.

When DNA detecting dyes or DNA detecting fluorogenic probes are added to PCR reactions, the fluorescent signal grows as the amplified DNA increases in concentration at each PCR cycle. When fluorescence is measured at each PCR cycle this process is known as real-time PCR (real-time PCR is often called quantitative PCR or qPCR) and it allows the amount of DNA target to be quantitated if a standard curve is run. Although simple intercalating fluorogenic dyes, such as SYBR Green can be used in qPCR, synthetic DNA probes are the best choice for rapid progress toward a functioning quantitative PCR assay. Unlike fluorogenic dyes, the sequence specificity of DNA probes allows detection of only the desired amplified sequence. The use of two different probes with two different color fluorescent labels allows built in controls that simplify the complexity of the test. The probes can be made using high throughput DNA synthesizers. DNA synthesis reagents are used to attach fluorescent quenching molecules to one end of the 20-30 mer strand (using modified solid supports) and fluorescent dyes to the opposite end of the strand (using phosphoramidite reagents). Alternatively, the fluorescent dye can be attached to a hexylamine modified oligo in a separate conjugation step.

There are two classes of fluorogenic DNA probe assays: hydrolysis probes and hybridization probes. Each assay uses probes that fluoresce in the presence of complementary DNA or RNA strands (fluorogenic probes), although the mechanisms of fluorescent signal generation are different.

The vast majority of probes used are hydrolysis probes (TAQMAN probes, ABI and Roche). TAQMAN probes are digested by Taq polymerase during the PCR and give excellent fluorescent signals because the fluor and quencher are cleaved from each other. Hybridization probes are best represented by the Molecular Beacons (see U.S. Pat. Nos. 5,925,517; 6,103,476; and 7,385,043, each expressly incorporated herein by reference in its entirety). Beacons are dual-labeled probes with a hairpin structure that positions the fluor and quencher molecules next to each other. Beacons have low fluorescence unless the complementary target strand is present as a result of amplification. It is better to use one primer in excess so that there is excess target strand at the end of the PCR (asymmetric PCR). Hybridization probes can also be designed in a two probe format where a "donor probe" (anchor probe) is labeled with a green emitting dye (fluorescein, Ex 490, Em 520) and the "acceptor probe" (emitter probe) has a red emitting fluor (Red 640, Em 640 nm) that is excited by the green emitting fluor by a process known as fluorescence resonance energy transfer (FRET) if both probes hybridize to the desired target DNA strand and the fluors are positioned next to each other. Red fluorescence occurs with 490 nm Ex only if both probes are hybridized.

Multiplexed Probes.

The large Stokes shift of the compounds of the invention described herein (e.g., benzo[c]xanthene compounds of formulae (I) and (II), their salts, active ester, acid/base forms, and tautomers) simplifies multiplexing where there is more than one indicating dye in a single reaction. For example, chloro SNFL-labeled oligonucleotide probes (Em=605) can be combined with hexachlorofluorescein (HEX)-labeled probes (Em=556) using a single excitation wavelength (540 nm). An advantage of the hybridization probes is that they can be present during quantitative PCR and are resistant to digestion. That allows (low resolution) melting curve analysis after PCR to distinguish single point mutations. There are a plethora of fluorogenic assay formats and all could take advantage of the large Stokes shift of the compounds of the invention simplifying detection in multiplexed assays. Commercial fluorogenic probe assays include two-probe fluorescence resonance energy transfer (FRET) assay (used in Roche LIGHTCYCLER system), Molecular Beacons (PHRI hybridization probes), minor groove binding (MGB) probes (Epoch/Nanogen/Elitech hybridization probes), TAQMAN probes (Roche/ABI hydrolysis probes), and INVADER assay (Hologic hydrolysis probes). The compounds of the invention can be incorporated into the above two-probe fluorescence resonance energy transfer systems and assays.

Two-Color Molecular Beacons.

The compounds of the invention described herein (e.g., benzo[c]xanthene compounds of formulae (I) and (II), their salts, active ester, acid/base forms, and tautomers) can be used to develop the hairpin-shaped Molecular Beacon probes for use with isothermal amplification assays (e.g., NASBA). In this embodiment, the quencher molecule DABCYL has been shown to quench fluorescent moieties having long wavelength emission spectra similar to the certain compounds of the invention. In this application, a yellow emitting fluor is easily multiplexed with the orange/red emitting chloro compounds of this invention.

Two-Color FRET Probes.

The probes of this invention work especially well in the "anchor probe"/"emitter probe" hybridization format. The current Red 640 label in the Roche LIGHTCYCLER probes has poor spectral overlap with the fluorescein emission (FIG. 8) whereas the chloro SNFL has much better overlap due to the large Stokes shift. Another yellow- or orange-labeled emitter probe (HEX or TAMRA) can be duplexed with the chloro SNFL probes. Sensitivity of the assay generally improves as spectral overlap increases.

Two-Color Hydrolysis Probes.

Hydrolysis probes like TAQMAN with yellow emitting labels are suitable for qPCR assays and are commercially available. These probes use special quencher molecules with long wavelength absorbance that overlaps with the emitted fluorescence of the label. For example, BLACK HOLE quencher (Biosearch) is available with three different structures that are designed to overlap (quench) fluors having emissions from green to red. BHQ2 is an effective quencher for yellow dyes and has been used successfully for HEX-labeled hydrolysis probes. HEX is hexachlorofluorescein (Ex 535/Em 556 nm). Dichlorodiphenylfluorescein, SIMA (HEX) exhibits virtually identical absorbance and emission spectra to HEX (Ex 538/Em 551 nm). SIMA (HEX) is much more stable to basic deprotection conditions than HEX and oligonucleotides can be deprotected using ammonium hydroxide at elevated temperatures and even ammonium hydroxide/methylamine (AMA) at room temperature or 65° C. for 10 minutes. YAKIMA YELLOW phosphoramidite (Ex 530/Em 549 nm) (U.S. Pat. No. 6,972,339) and synthetic probes using this dye are available from Eurogentec. Probes containing HEX and BLACK HOLE Quenchers are commercially available (e.g., Integrated DNA Technologies (IDT), Coralville Iowa, and Biosearch, Novato, Calif.).

Thus, in other aspects of the invention, fluorogenic probes prepared from the compounds of the invention described herein (e.g., benzo[c]xanthene compounds of formulae (I) and (II), their salts, active ester, acid/base forms, and tautomers) are provided. The fluorogenic probes of the invention can be used in the methods described above and known in the art.

In one embodiment, the invention provides a fluorogenic probe prepared from a compound of the invention and an oligonucleotide.

In one embodiment, representative fluorogenic probes of the invention have the formula: $F_1$—$OGN_1$, where $F_1$ is a compound of the invention, $OGN_1$ is an oligonucleotide suitable for use as hybridization probe. These probes can be used as emitter probes in combination with anchor probes having the formula: $F_2$—$OGN_2$, where $F_2$ is a fluorescent compound having an emission spectrum that overlaps the absorption spectrum of $F_1$, and $OGN_2$ is an oligonucleotide suitable for use as hybridization probe, such that on hybridization fluorescence resonance energy transfer occurs from $F_2$ to $F_1$ (e.g., $OGN_2$—$F_2$:$F_1$—$OGN_1$). Representative fluorogenic probes of the invention having the formula $F_1$—$OGN_1$ can also be used as anchor probes in combination with emitter probes having the formula: $F_3$—$OGN_3$, where $F_3$ is a fluorescent compound having an absorption spectrum that overlaps the emission spectrum of $F_1$, and $OGN_3$ is an oligonucleotide suitable for use as hybridization probe, such that fluorescence resonance energy transfer occurs from $F_1$ to $F_3$ on hybridization (e.g., $OGN_1$—$F_1$:$F_3$—$OGN_3$).

In another embodiment, representative fluorogenic probes of the invention have the formula: $F_1$—OGN—$F_2$, where $F_1$ is a compound of the invention, OGN is an oligonucleotide suitable for use as hybridization probe, and $F_2$ is a fluorescent compound having an emission spectrum that overlaps the absorption spectrum of $F_1$ such that fluorescence resonance energy transfer occurs from $F_2$ to $F$ in solution, and fluorescence resonance energy transfer is lost on hybridization. In another embodiment, representative fluorogenic probes of the invention have the formula: $F_1$—OGN-$F_3$, where $F_1$ is a compound of the invention, OGN is an oligonucleotide suitable for use as hybridization probe, and $F_3$ is a fluorescent compound having an absorption spectrum that overlaps the emission spectrum of $F_1$ such that fluorescence resonance energy transfer occurs from $F_1$ to $F_3$ in solution, and fluorescence resonance energy transfer is lost on hybridization.

In a further embodiment, the invention provides fluorogenic probes prepared from a compound of the invention, a suitable quencher, and an oligonucleotide. Representative fluorogenic probes of the invention have the formula: $F_1$—OGN-Q, where $F_1$ is a compound of the invention, OGN is an oligonucleotide suitable for use as a Molecular Beacon or TAQMAN probe, and Q is a quencher effective to quench $F_1$ fluorescence in solution, but not on hybridization.

In other aspects, methods for using the fluorogenic probes of the invention are provided. The methods that include the use of the fluorogenic probes of the invention include those described above and known in the art.

In other aspects, kits including the fluorogenic probes of the invention are provided.

DNA Synthesis Reagents

Active esters (e.g., NHS) of the compounds of the invention described herein (e.g., benzo[c]xanthene compounds of formulae (I) and (II)) can be used to prepare oligonucleotide conjugates. Current conjugation reactions are labor intensive and require careful handling. Labels can be introduced during automated DNA synthesis by converting them to phosphoramidite reagents or synthesizing modified solid supports for DNA synthesis. Glen Research (Sterling, Va.) sells CPG solid supports and phosphoramidite reagents to introduce fluorescent labels (Gig Harbor Green, Yakima Yellow, Redmond Red) and ECLIPSE Quencher. The reagents allow versatile synthesis of FRET probes for use as hydrolysis or hybridization probes. The methods are published and the reagents are patented. In particular, YAKIMA YELLOW has ideal properties as a matched set for the large Stokes shift SNFL compounds of the invention.

The compounds of the invention can be used in dual-probe kits and methods as either the emitter or the acceptor, depending on the second probe. For example, in one embodiment, YAKIMA YELLOW can be paired with a compound of the invention (e.g., 2-chloro SNFL and 2,4-dichloro SNFL) for use FRET kits and methods in which YAKIMA YELLOW is the anchor and the SNFL compound is the emitter; and in another embodiment, a compound of the invention (e.g., 2-chloro SNFL and 2,4-dichloro SNFL) can be paired with RED 640 in FRET kits and methods in which the SNFL compound is the anchor and RED 640 is the emitter. It will be appreciated that other combinations including the compounds of the invention are with the scope of the invention.

Instrumentation for Measuring Chloro SNFL Emission.

The large Stokes shift of the compounds of the invention simplifies multiplexing where there is more than one indicating dye in a single reaction. For example, chloro SNFL-labeled oligonucleotide probes (Em=605) can be combined with hexachlorofluorescein (HEX) labeled probes (Em=556) using a single excitation wavelength (540 nm). A fluorescence detector with optical filters tuned for the chloro SNFL spectral properties is available (pH1000, Blood Cell Storage Inc., Seattle Wash., see U.S. Pat. No. 7,680,460 describing LED excitation/photodiode detection). The large Stoke's shift of the chloro SNFL compounds of the invention enables use of this single excitation, two channel detector system. These optical reading devices can be coupled with precise thermal control for DNA amplification and melting curve analysis of the amplified sequences can be used to identify specific DNA sequences by monitoring changes in fluorescence versus temperature. Endpoint assays will eliminate the need for careful temperature control.

Alkyl Carboxylic Acid Compounds for Fluorescent Labeling

In another aspect, the invention provides alkyl carboxylic acid compounds that, like their amine counterparts, are useful for fluorescent labeling. In these compounds, the "linker arm" is derived from an alkyne that does not include an amine group, but rather includes a carboxylic acid group (or a latent carboxylic acid group).

In this aspect, the alkyne compounds useful in the invention have the formula

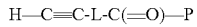

wherein L is a linker moiety intermediate the alkyne group and the carbonyl group of the carboxylic acid (or the protected carboxylic acid), and wherein P is hydroxy or a carboxylic acid protecting group that is ultimately cleaved to provide a carboxylic acid group, which can be further elaborated as described below.

Linker moiety L serves as a spacer between the alkyne group and the carbonyl group. Linker moiety L has a length not exceeding the length of a normal alkyl chain of 25 carbons. Suitable linker moieties L include from one to about fifty (50) atoms selected from carbon, nitrogen, oxygen, hydrogen, and halogen. Representative L groups include alkylene groups (e.g., —(CH$_2$)$_n$—, where n is 1-12), phenylene groups (e.g., o-, m-, and p-C$_6$H$_4$—), and alkyleneoxide groups (e.g., ethylene oxide, —(CH$_2$CH$_2$O)$_m$—, where m is 1-5). In one embodiment, L is —(CH$_2$)—.

Representative P groups include carboxylic acid protecting groups known in the art. Suitable carboxylic acid protecting groups are described in T. W. Greene and P. G. Wuts, PROTECTIVE GROUPS IN ORGANIC CHEMISTRY, (Wiley, 2nd ed. 1991), expressly incorporated herein by reference in its entirety. In one embodiment, P is OR', where R' is a substituted or unsubstituted alkyl (e.g., C1-C6) or aryl (e.g., C6-C10) group. In this embodiment, the alkyne is an ester hydrolyzable to its corresponding carboxylic acid.

In one embodiment, the alkyne is H—C≡C—CH$_2$CH$_2$—C(=O)OCH$_3$ (i.e., L is CH$_2$CH$_2$ and P is OCH$_3$).

As noted above, the alkyne compounds are useful for making the fluorescent dye compounds of the invention. In the fluorescent dye compounds of the invention, the linker arm is derived from the alkyne described above. Fluorescent dye compounds of the invention are described in detail below. In one embodiment, the linker arm is —(CH$_2$)$_n$CO$_2$H, where n is 3-8 (which may exist in salt form depending on conditions).

In certain embodiments of the invention, the fluorescent dye compounds of the invention are functionalized to provide labeling agents. In these embodiments, the fluorescent dye compound's linker arm is functionalized by reaction of the linker arm's carboxylic acid group. Suitable functionalization provides functionalized fluorescent dye compounds that are effective for reaction with a variety of materials including biomolecules (e.g., oligonucleotides, proteins, peptides).

In another aspect, the invention provides labeling agents having the formula

Fluorophore aryl moiety-CH$_2$CH$_2$-L-CO$_2$H its salts, active esters, acid/base forms, and tautomers, wherein "Fluorophore aryl moiety" refers to the fluorescent dye compound fluorescent core to which is attached the functionalized linker arm (i.e., —CH$_2$CH$_2$-L-CO$_2$H), wherein L is a linker moiety intermediate the methylene group and the carbonyl group (and is the same as L in the alkyne compounds described above).

The alkyl carboxylic acid compounds of the invention are prepared by coupling suitable alkyne compounds described above with halo-resorcinol derivatives as described herein for producing the alkyl amine compounds of the invention.

Each reference cited herein is incorporated by reference in its entirety.

The following examples are provided for the purpose of illustrating, not limiting, the invention.

EXAMPLES

Example 1

The Preparation and Properties of a Representative Compound of the Invention: BCSI-3

In this example, the preparation and properties of a representative compound of the invention, BCSI-3, is described. The preparation is illustrated schematically in FIG. 1.

General Procedures.

All TLC was run with Sigma-Aldrich silica gel plates (catalog #Z193275). $^1$H NMR were obtained on a Bruker 300 MHz spectrometer in dimethyl sulfoxide-d$_6$) at room temperature. Chemical shifts (ppm) were referenced to dimethyl sulfoxide (2.49 ppm). All solvents, reagents and silica gel for column chromatography were purchased from Sigma-Aldrich.

N-[3-2,4-Dimethoxyphenyl)prop-2-yn-1-yl]-2,2,2-trifluoroacetamide (2)

A solution consisting of anhydrous DMF (2.0 ml), anhydrous triethylamine (3.9 ml) and propargyl trifluoroacetimide (5.3 g, 35.1 mmol) was deoxygenated by bubbling a stream of argon through the solution for 20 min. This solution was then added to a mixture of 1-Iodo-2,4-dimethoxybenzene (4.9 g, 18.6 mmol), CuI (37 mg, 0.21 mmol) and tetrakis[triphenylphosphine]-palladium[0] (120 mg, 0.10 mmol). The resulting mixture was stirred under an argon atmosphere for 24 hrs. The reaction mixture was diluted with 50 ml of ethyl acetate and washed with water (3×50 ml). The organic phase was dried over sodium sulfate, filtered and evaporated. The residue was purified by silica gel chromatography eluting with a gradient of 10-25% ethyl acetate in hexane. The product fractions were evaporated and the residue was crystallized from methanol-water: 2.3 g (43% yield); TLC (50/50, ethyl acetate/hexane), R$_f$=0.59; $^1$H NMR (DMSO-d$_6$) δ 10.05 (1H, br s, N—H), 7.29 (1H, d, J=8.4 Hz, aromatic-H), 6.59 (1H, d, J=2.4 Hz, aromatic-H), 6.51 (1H, dd, J=8.4 & 2.4 Hz, aromatic-H), 4.25 (2H, s, methylene-H), 3.79 and 3.78 (6H, 2×s, methoxy-Hs).

N-[3-2,4-dimethoxyphenyl)propyl]-2,2,2-trifluoroacetamide (3)

Absolute ethanol (40 ml) was carefully added to a 150-ml round-bottom flask containing 2 (2.2 g, 7.7 mmol) and 5% Pd/C (0.40 g) under an argon atmosphere. Ammonium formate (6.5 g, 103 mmol) was added and the resulting mixture was refluxed for 40 min. The reaction mixture was filtered through Celite and the filter cake was rinsed with 100 ml of methanol. The filtrate was evaporated to dryness and the residue was suspended in 30 ml of water and extracted with ethyl acetate (2×40 ml). The pooled extracts were dried over sodium sulfate, filtered and evaporated affording a homogenous oil, which transformed into a crystalline solid upon overnight storage in a standard commercial freezer: 2.0 g (89% yield). TLC (50/50, ethyl acetate/hexane), R$_f$=0.75.

N-[3-(2,4-Dihydroxyphenyl)propyl]-2,2,2-trifluoroacetamide (4)

A suspension of 3 (1.06 g, 3.6 mmol) was stirred in 15 ml of a 1M solution of boron tribromide in methylene chloride for 45 min. at room temperature. Ice-cold methanol (5 ml) was carefully added drop-wise and the resulting solution was evaporated to dryness. The residue was purified by silica gel chromatography eluting with 50/50, ethyl acetate/hexane. The pure product fractions were evaporated affording a homogenous oil: 0.76 g (79% yield). $^1$H NMR (DMSO-d$_6$) δ 9.39 (1H, br t, trifluoroacetimido, N—H), 9.11 and 8.96 (2H, 2×s, phenol-Hs), 6.80 (1H, d, J=8.5 Hz, aromatic-H), 6.27 (1H, d, J=2.5 Hz, aromatic-H), 6.13 (1H, dd, J=8.4 & 2.5 Hz, aromatic-H), 3.16 (2H, m, methylene-H), 2.40 (2H, t, J=7.5 Hz, methylene-H), 1.66 (2H, m, methylene-H).

2-(2,4-Dihydroxy-5-{3-[(trifluoroacetyl)amino] propyl}benzoyl)benzoic acid (5)

A mixture of 4 (0.56 g, 2.1 mmol), phthalic anhydride (0.32 g, 2.2 mmol) and aluminum chloride (0.80 g, 6.0 mmol) was stirred in anhydrous dichloroethane (under argon) for 20 hr.

The dichloroethane solvent was decanted away and the solid residue was dissolved in 50 ml of ethyl acetate and washed with 50 ml of water. The pH of the aqueous phase was adjusted to approximately pH 3 by addition of acetic acid and then extracted with ethyl acetate (2×50 ml). The combined organic extracts were dried over sodium sulfate, filtered and evaporated. The residue was purified by silica gel chromatography eluting with a gradient of 25-0% hexane in ethyl acetate. The pure product fractions were evaporated affording a homogenous oil: 0.32 g (34% yield).

2-[5-(3-Aminopropyl)-2,4-dihydroxybenzoyl]benzoic acid (6)

Compound 5 (167 mg, 0.38 mmol) was incubated in concentrated ammonium hydroxide (4.0 ml) for 1.0 hr at 50 degrees C. The resulting solution was evaporated to dryness and the residue was precipitated from methanol-diethyl ether: 96-mg (74% yield). TLC (50/48/2, ethyl acetate/methanol/acetic acid), $R_f$=0.50; $^1$H NMR (DMSO-$d_6$) δ 7.78 (1H, m, aromatic-H), 7.43 (2H, m, aromatic-Hs), 7.18 (1H, m, aromatic-H), 6.95 and 6.26 (2H, 2×s, aromatic-Hs), 2.37 (2H, t, J=6.6 Hz, methylene-Hs), 1.68 (2H, m, methylene-Hs). Note—An additional methylene peak (2Hs) is expected to be hidden under the large water peak covering the range 3.8-3.1 ppm.

Reaction of 6 with Succinic Anhydride (Compound 7).

To a suspension of 6 (150 mg, 0.44 mmol) in a solution of anhydrous DMF (1.0 ml) and anhydrous triethylamine (0.34 ml) was added succinic anhydride (52 mg, 0.52 mmol). The reaction mixture was stirred for 18 hr at room temperature. The solvents were evaporated off and the residue was purified by silica gel chromatography eluting with 50/50, ethyl acetate/methanol. The UV-active column band was isolated and evaporated affording a homogeneous oil: 150 mg (77% yield).

BCSI-3 (Compound 1).

A mixture of 7 (150 mg, 0.34 mmol) and 7-chloro-1,6-dihydroxynapthalene (100 mg, 0.51 mmol), prepared as described in U.S. Patent Application Publication No. US 2006/0204990, was stirred in a solution of trifluoroacetic acid (1.4 ml)/methanesulfonic acid (0.50 ml) for 2 hr. at 50 degrees C., followed by continued stirring at room temperature for 20 hr. The crude product was filtered and dried after precipitation by addition of 6 ml of water to the reaction mixture. The crude product was then purified by silica gel chromatography eluting with 48/48/4, methanol/methylene chloride/triethylamine as the mobile phase. The pure product fractions were evaporated to dryness and the residue was suspended in water. Sodium hydroxide solution (1 M) was added drop wise to dissolve the material before addition of 1 M hydrochloric acid solution to re-precipitated the pure dye product. The solid was filtered, rinsed with water and dried: 95 mg (49% yield). TLC (48/48/4, methylene chloride/methanol/triethylamine), $R_f$=0.56; $^1$H NMR (DMSO-$d_6$) δ 8.04 (1H, dd, J=6.6 & 2.7 Hz, aromatic-H), 7.76 (3H, m, aromatic-Hs), 7.40 (1H, d, J=9.0 Hz, aromatic-H), 7.35 (1H, s, aromatic-H), 7.26 (1H, dd, J=6.3 & 0.90 Hz, aromatic-H), 6.99 (1H, s, aromatic-H), 6.61 (1H, d, J=6.9 Hz, aromatic-H), 6.50 (1H, s, aromatic-H), 2.92 (2H, m, methylene-Hs), 2.50 (4H, m, methylene-Hs), 2.24 (2H, m, methylene-Hs), 1.46 (2H, m, methylene-Hs).

The absorbance spectra of BCSI-3 are shown in FIGS. 2-4. FIGS. 2-4 compare the absorbance spectra of EBIO-3 and BCSI-3 at pH 9.5, 7.4, and 4.5 (borate buffer, phosphate buffered saline, and acetate buffer), respectively. The wavelength spectra are equivalent for the two dyes at all three pHs (high, mid, and low).

The purity (HPLC) was determined by UV/Vis absorption for BCSI-3 was >99% at 530 nm and 95% at 270 nm.

The $^1$H NMR spectrum of BCSI-3 was consistent with the dye's structure.

The pKa of BCSI-3 was determined by an absorbance assay with controlled pH buffers. The pKa results for BCSI-3 and EBIO-3 are shown in FIGS. 5 and 6, respectively. The two pKa values are 6.64 (BCSI-3) and 6.61 (EBIO-3).

A photobleaching degradation curve for EBIO-3 and BCSI-3 was constructed utilizing fluorescent light exposure and measuring the absorption at 530 nm to quantify functional dye. Identical concentrations of both dyes, 7.9 μM, were exposed to continuous fluorescent light (34 W Philips Hg bulb) from a distance of 16 inches for 3 days. The results are shown in FIG. 7. At 73.5 hours the two dyes had degraded 64% and the degradation is within 5.6% of each other. A control set of dyes protected from light showed unchanged absorptions at 530 nm.

Example 2

The Preparation and Fluorescent Properties of a Representative Fluorophore-Protein Conjugate: BCSI-3/HSA In this example, the preparation and properties of a representative fluorophore-protein conjugate, BCSI-3/HSA, is described. The preparation is illustrated schematically in FIG. 8.

BCSI-3, prepared as described in Example 1, was conjugated to recombinant human serum albumin (rHSA) by an EDC (1-[3-(dimethylamino)propyl]-3-ethyl-carbodiimide hydrochloride) activation reaction. The dye was activated by a 1 hour reaction with EDC in an 83% DMF (N,N-dimethylformamide) and 17% PBS (phosphate buffered saline 150 mM sodium chloride, 50 mM sodium phosphate, pH 7.4) mixed solvent. The EDC is at a 5 times molar excess to the dye.

The activated dye was mixed with a 13.6 mg/ml rHSA solution a pH 8.5 carbonate buffer (100 mM sodium carbonate). The dye was at a 25 times molar excess to the protein. The conjugation reaction is incubated overnight protected from light.

Purification of the conjugate from free dye was carried out by ultrafiltration with PBS and a 10,000 MW cutoff (Amicon YM10, Millipore). The low molecular weight free dye was removed from the higher molecular weight conjugate.

Conjugation by this method yielded a nominal 2 dye per rHSA conjugate.

EBIO-3 has a 3 carbon atom long carboxylic acid linker arm. This linker length allows an intramolecular ester to form with the adjacent phenol on the dye ring structure. This relatively stable 6-member lactone forms as an intermediate that likely protects the EBIO-3 dye from the hydrolysis during pH 8.5 reaction with lysine on the HSA. EDC activated EBIO-3 routinely gives 2:1 loading level of dye:HSA from an offering ratio of 5:1. In contrast the BCSI-3 dye has an 8 atom long linker arm that cannot form the stable 6-member lactone ring structure. More rapid hydrolysis of the EDC activated BCSI-3 dye at pH 8.5 leads to lower reaction efficiency in the conjugation reaction. EDC activated BCSI-3 routinely gave 2:1 loading level of dye:HSA from an offering of 25:1. The excess dye was easily removed from the labeled protein by size exclusion chromatography or stirred cell ultrafiltration. More amide bond formation occurred with EBIO-3 than with BCSI-3. More EDC ester hydrolysis occurred with BCSI-3 than with EBIO-3. Therefore more offered dye was needed for BCSI-3 to obtain similar loading.

FIG. 9 is a graph illustrating loading ratio of a representative fluorescent species (BCSI-3) to a representative protein (rHSA) as a function of offering ratio (BCSI-3/rHSA). FIG. 10 compares fluorescent ratio signal as a function of test buffer pH for representative fluorophore-protein conjugates (EBIO-3/HSA and BCSI-3/HSA conjugates).

Example 3

The Preparation and Properties of a Representative Compound of the Invention

Fluorescein Analog (GR Dye)

In this example, the preparation and properties of a representative compound of the invention, a fluorescein analog (GR dye), is described. The preparation is illustrated schematically in FIG. 11.

General Procedures.

All TLC was run with Sigma-Aldrich silica gel plates (catalog #Z193275). $^1$H NMR were obtained on a Bruker 300 MHz spectrometer in dimethyl sulfoxide-$d_6$) at room temperature. Chemical shifts (ppm) were referenced to dimethyl sulfoxide (2.49 ppm). All solvents, reagents and silica gel for column chromatography were purchased from Sigma-Aldrich.

Preparation.

Synthesis of compound 7 uses succinic anhydride to acylate the aminopropyl linker in 6 to give the succinamide. A presumed 1.73 mmol of compound 6 was suspended in 4.5 mL of dry DMF. Dry TEA (1.6 mL) was added followed by succinic anhydride (243 mg). After 1 hour there was still some starting material by HPLC. Another 1.6 mL of TEA and 243 mg of succinic anhydride were added and the mix was stirred for another hour before removal of solvents on the rotavap and drying the residue under high vacuum overnight. The residue was stirred in 0.5 M sodium hydroxide for 45 minutes and then the solution was acidified to about pH 3 by addition of conc. HCl. The solution was extracted with ethyl acetate (3×50 mL). The organic extracts were dried over sodium sulfate, filtered and evaporated. The residue was purified by silica gel column, elution with 1:1/hexanes:ethyl acetate. The pure fractions were pooled and evaporated to give 7 as a solid foam. Yield=350 mg (49%). Alternatively compound 7 was isolated using silica gel chromatography and a gradient of 10-50% methanol/in methylene chloride (2% triethylamine). Pure fractions eluted in a yellow band and were pooled and evaporated to give a hygroscopic beige solid as the bis-triethylammonium salt. $^1$H NMR δ (DMSO-$d_6$) 7.79 (2H, m, amide and aromatic-H), 7.42 (2H, m, aromatic-Hs), 7.13 (1H, d, m, aromatic-H), 6.84 (1H, s, aromatic-H), 6.27 (1H, aromatic-H), 2.4-2.1 (6H, m, methylene-Hs), 1.44 (2H, m, methylene-Hs). Triethylammonium peaks were observed at 2.6 (12H, m, methylene-Hs) and 0.975 (18H, J=7.2 Hz).

A solution of 10.9 mg (0.0176 mmol) of Compound 7 (triethylammonium salt, MW=617) in 0.372 mL trifluoroacetic acid and 0.132 mL of methanesulfonic acid was stirred in a 5 mL round bottom flask. 33.7 mg of resorcinol (1,3-dihydroxybenzene, 0.306 mmol) was added and the mixture turned a deep purple as the solid dissolved over a few minutes. The mixture was capped and stirred overnight at ambient temperature, then quenched by adding to a 60 mL separatory funnel containing 1 gram of ice. An additional 3 mL of water was used to rinse the flask into the separatory funnel and 10 mL of saturated sodium bicarbonate was carefully added. The aqueous phase was extracted with 3×12 mL of diethyl ether to remove excess resorcinol, then acidified to pH 2 with 1 mL of concentrated hydrochloric acid. The aqueous phase was extracted with 3×12 mL of ethyl acetate and the combined organics were dried over magnesium sulfate and concentrated by rotary evaporation to give 11.1 mg of crude product as an orange oil. TLC (1:1/methanol:methylene chloride with 2% triethylamine) showed one major yellow spot ($R_f$=0.35) with green fluorescence under long wavelength UV irradiation (365 nm). The crude product was dissolved 0.5 mL of the TLC solvent and applied to a 2×18 cm silica column packed with (1:4/methanol:methylene chloride with 2% triethylamine). After collecting a fast running yellow impurity band, the desired product was eluted using the TLC solvent. The pure fractions were combined and concentrated by rotary evaporation to give 17.3 mg of the target compound as a yellow solid (166% yield) likely mixed with silica from the column purification. Percent dye content was determined to be 17.7% as described below (yield was 3.06 mg, 29%).

Characterization.

Structure was confirmed by mass spec analysis. A Thermo Scientific LTQ mass spectrometer was used with electrospray ionization and positive and negative ion detection. Negative ion detection showed the molecular ion as the major peak MS (ESI) calcd for $C_{27}H_{23}NO_8$ (M-H) 489.14. Found 489.3. $^1$H NMR ($d_6$-DMSO) 8.0 (d, J=7.5 Hz, 1H), 7.76 (m, 2H), 7.25 (d, J=7.5 Hz, 1H), 7.76 (s, 1H), 6.69 (d, J=1.8 Hz, 1H), 6.53 (m, 2H), 6.38 (s, 1H), 2.93 (m, 2H, partially obscured by triethylamonium salt at 3.03 ppm), 2.37 (m, 4H), 2.23 (m, 2H), 1.39 (m, 2H), 1.18 (m due to triethylammonium salt).

Absorbance and Fluorescence Measurements.

Percent dye content was determined by comparison with a fluorescein reference standard (Aldrich cat no. F2456), assuming similar extinction coefficient. A 4 mg/mL solution of the yellow solid from above was prepared in DMSO and diluted in pH 8.5 carbonate buffer (0.1 M) to give an expected 20 μM solution. Absorbance maximum (496 nm) was found to be 17.7% of 20 μM of fluorescein (absorbance maximum 490 nm). A corrected 20 μM solution of the dye was analyzed for fluorescence on a Bio-Tek plate reader (Excitation 485/20 nm, Emission 528/20 nm). Fluorescent signal of the dye was 98% of the fluorescein reference standard.

While illustrative embodiments have been illustrated and described, it will be appreciated that various changes can be made therein without departing from the spirit and scope of the invention.

The invention claimed is:

1. A compound having the formula (III) or (IV):

(III)

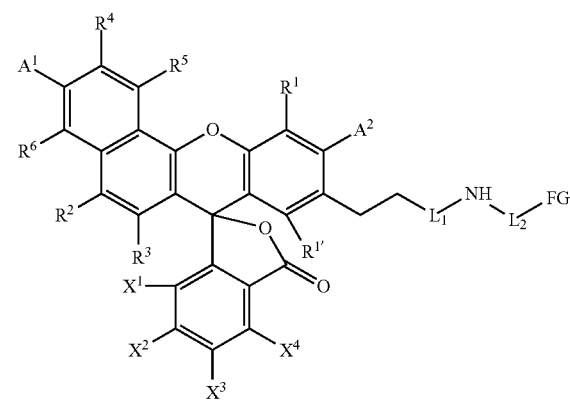

-continued (IV)

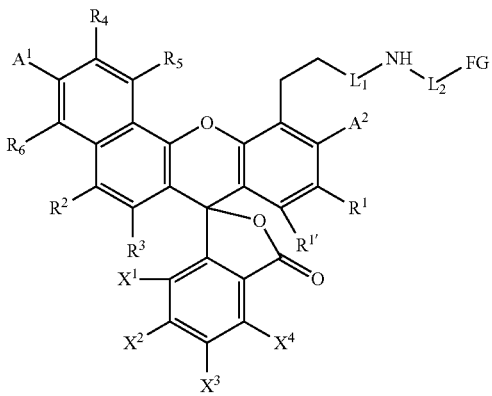

their salts, active esters, acid/base forms, and tautomers, wherein $A^1$ and $A^2$ are independently selected from hydroxy, amino, mono- and dialkyl amino, protected hydroxy, protected amino, protected mono- and dialkyl amino, or when $A^1$ or $A^2$ is amino, mono- and dialkyl amino, $A^1$ and/or $A^2$ taken together with $R^2$ and/or $R^4$ (for $A^1$) or with $R^1$ (for $A^2$) and the atoms to which they are attached form a 5- or 6-membered nitrogen-containing ring;

$R^{1'}, R^1, R^2, R^3, R^4$, and $R^5$ are each independently selected from the group consisting of hydrogen, halogen, cyano, trifluoromethyl, $(C_1-C_8)$alkyl, $(C_1-C_8)$alkylthio and $(C_1-C_8)$alkoxy, aryl, and heteroaryl;

$R^6$ is halogen;

$X^1, X^2, X^3$, and $X^4$ are each independently selected from the group consisting of hydrogen, halogen, cyano, trifluoromethyl, $(C_1-C_8)$alkyl, $(C_1-C_8)$alkoxy, $(C_1-C_8)$alkylthio, $(C_2-C_8)$alkenyl, $(C_2-C_8)$alkynyl, aryl, aryl $(C_1-C_4)$alkyl, heteroaryl, $SO_3H$ and $CO_2H$, wherein the alkyl portions of any of $R^{1'}$ and $R^1-R^6$ and $X^1-X^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms;

and wherein the aryl or heteroaryl portions of any of $R^{1'}$ and $R^1-R^6$ and $X^1-X^4$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy;

wherein $L_1$ has a length not exceeding the length of a normal alkyl chain of 25 carbons and comprises from one to about 50 atoms, wherein $L_2$ has a length not exceeding the length of a normal alkyl chain of 25 carbons and comprises from one to about 50 atoms, and wherein FG is a functional group reactive toward and capable of covalently coupling the fluorescent dye compound to a suitably reactive material.

2. A compound having the formula:

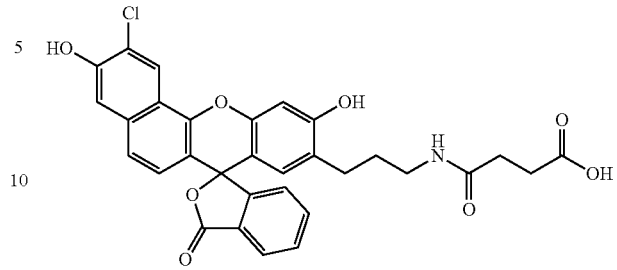

its salts, active esters, acid/base forms, and tautomers.

3. A compound having the formula (III) or (IV):

(III)

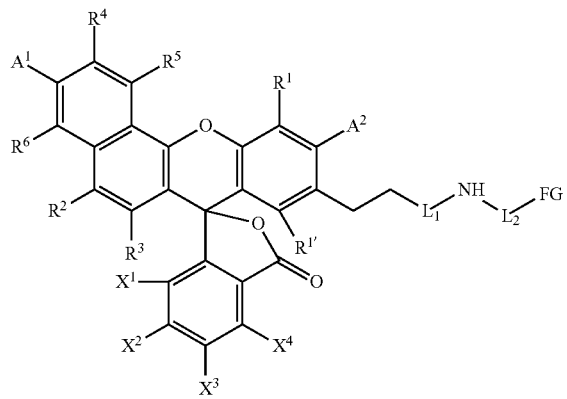

(IV)

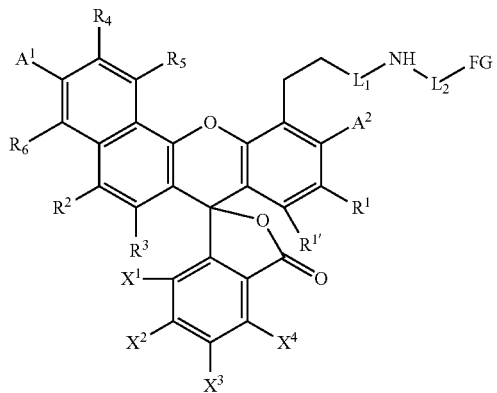

their salts, active esters, acid/base forms, and tautomers, wherein $A^1$ and $A^2$ are independently selected from hydroxy, amino, mono- and dialkyl amino, protected hydroxy, protected amino, protected mono- and dialkyl amino, or when $A^1$ or $A^2$ is amino, mono- and dialkyl amino, $A^1$ and/or $A^2$ taken together with $R^2$ and/or $R^4$ (for $A^1$) or with $R^1$ (for $A^2$) and the atoms to which they are attached form a 5- or 6-membered nitrogen-containing ring;

$R^{1'}, R^1, R^2, R^3$, and $R^5$ are each independently selected from the group consisting of hydrogen, halogen, cyano, trifluoromethyl, $(C_1-C_8)$alkyl, $(C_1-C_8)$alkylthio and $(C_1-C_8)$alkoxy, aryl, and heteroaryl;

$R^4$ and $R^6$ are halogen;

$X^1$, $X^2$, $X^3$, and $X^4$ are each independently selected from the group consisting of hydrogen, halogen, cyano, trifluoromethyl, $(C_1-C_8)$alkyl, $(C_1-C_8)$alkoxy, $(C_1-C_8)$alkylthio, $(C_2-C_8)$alkenyl, $(C_2-C_8)$alkynyl, aryl, aryl $(C_1-C_4)$alkyl, heteroaryl, $SO_3H$ and $CO_2H$, wherein the alkyl portions of any of $R^{1'}$ and $R^1$-$R^6$ and $X^1$-$X^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and wherein the aryl or heteroaryl portions of any of $R^{1'}$ and $R^1$-$R^6$ and $X^1$-$X^4$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy;

wherein $L_1$ has a length not exceeding the length of a normal alkyl chain of 25 carbons and comprises from one to about 50 atoms, wherein $L_2$ has a length not exceeding the length of a normal alkyl chain of 25 carbons and comprises from one to about 50 atoms, and wherein FG is a functional group reactive toward and capable of covalently coupling the fluorescent dye compound to a suitably reactive material.

4. The compound of claim 1, wherein $R^6$ is chloro.
5. The compound of claim 3, wherein $R^4$ is chloro.
6. The compound of claim 3, wherein $R^6$ is chloro.
7. The compound of claim 3, wherein $R^4$ and $R^6$ are chloro.

\* \* \* \* \*